(12) United States Patent
Zuluaga

(10) Patent No.: US 8,509,880 B1
(45) Date of Patent: Aug. 13, 2013

(54) HANDHELD PORTABLE EXAMINATION DEVICE FOR DIAGNOSTIC USE

(75) Inventor: Andrés Felipe Zuluaga, Houston, TX (US)

(73) Assignee: Remicalm, LLC, Houston, TX (US)

( * ) Notice: Subject to any disclaimer, the term of this patent is extended or adjusted under 35 U.S.C. 154(b) by 1138 days.

(21) Appl. No.: 12/322,598

(22) Filed: Feb. 4, 2009

Related U.S. Application Data

(60) Provisional application No. 61/063,755, filed on Feb. 6, 2008.

(51) Int. Cl.
*A61B 6/00* (2006.01)

(52) U.S. Cl.
USPC .......................................... 600/476; 600/472

(58) Field of Classification Search
USPC ................... 600/476, 478, 111–113; 356/12, 356/16, 460, 456, 487
See application file for complete search history.

(56) References Cited

U.S. PATENT DOCUMENTS

| | | | | |
|---|---|---|---|---|
| 5,647,368 A * | 7/1997 | Zeng et al. | ..................... | 600/476 |
| 6,110,106 A * | 8/2000 | MacKinnon et al. | ......... | 600/181 |
| 2002/0105640 A1 * | 8/2002 | Deck et al. | ..................... | 356/301 |
| 2002/0183622 A1 * | 12/2002 | Zuluaga et al. | ................ | 600/476 |
| 2004/0220451 A1 * | 11/2004 | Gravenstein et al. | ......... | 600/139 |
| 2007/0038117 A1 * | 2/2007 | Bala | ............................... | 600/476 |
| 2007/0097319 A1 * | 5/2007 | McKay et al. | ..................... | 353/7 |
| 2008/0030732 A1 * | 2/2008 | Yaroslavsky et al. | ......... | 356/369 |

\* cited by examiner

*Primary Examiner* — Tse Chen
*Assistant Examiner* — Joel F Brutus
(74) *Attorney, Agent, or Firm* — Elizabeth R. Hall

(57) ABSTRACT

A portable medical examination device used for cancer detection using tissue illumination with radiation of a certain wavelength band to provide the operator with either reflected images of the tissue or by inducing visible fluorescence of the irradiated tissue. The medical examination device has an illumination source transmitting a light beam through a first lens unit to condition the light beam; a fiber optic bundle including an excitation fiber and an image fiber, wherein the excitation fiber delivers the conditioned light from the first lens unit to a tissue to be examined and wherein the image fiber directs the light emanating from the illuminated tissue to a second lens unit; and an angularly adjustable visualization unit, wherein a light beam conditioned by the second lens unit is visualized by the device operator and/or captured by an image capture device.

39 Claims, 13 Drawing Sheets

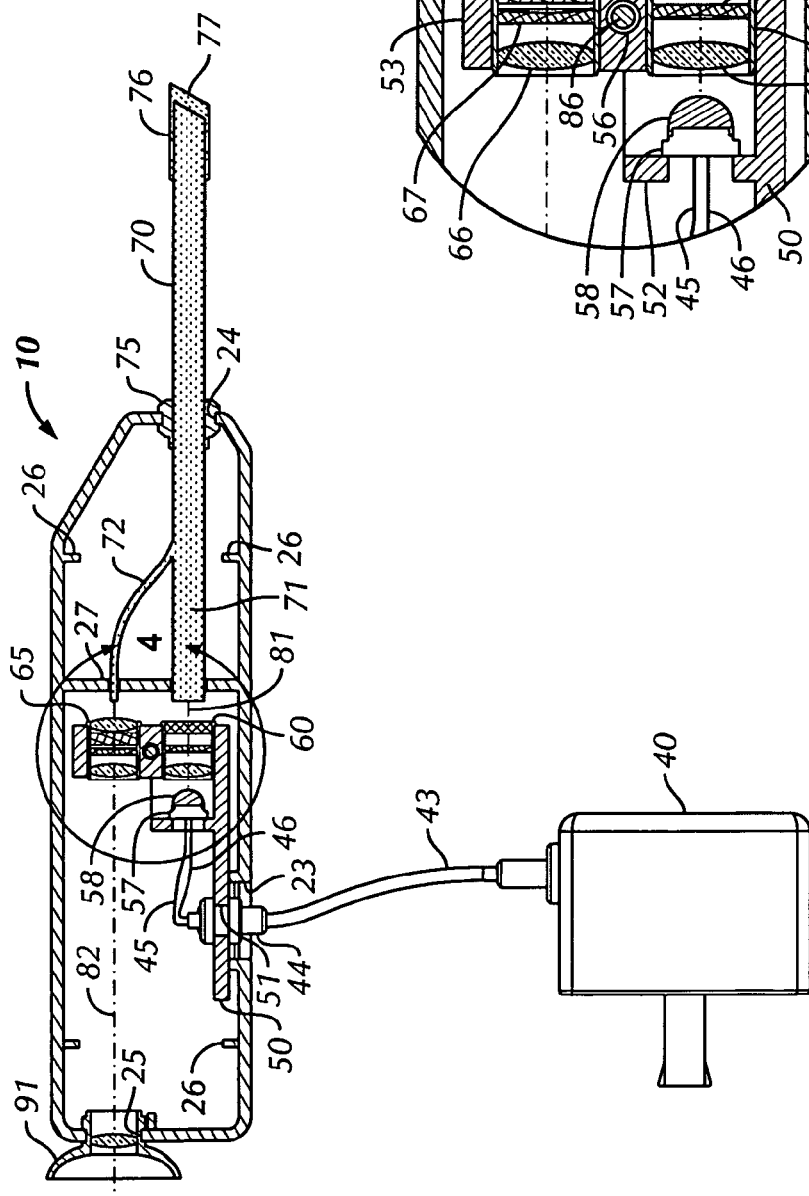
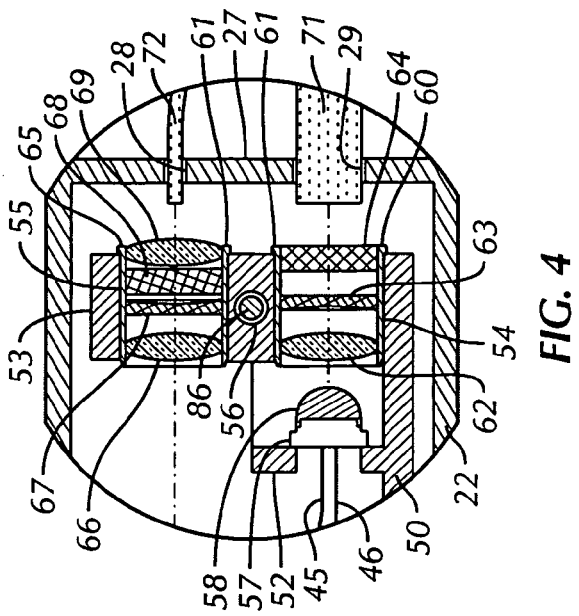

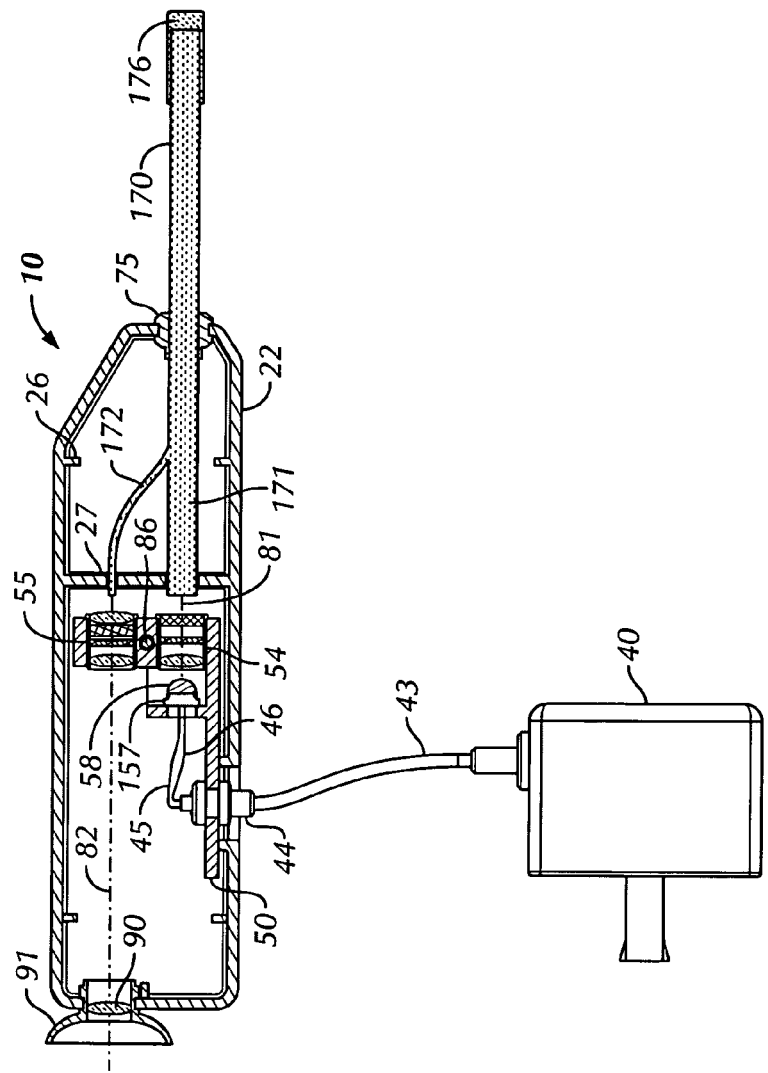
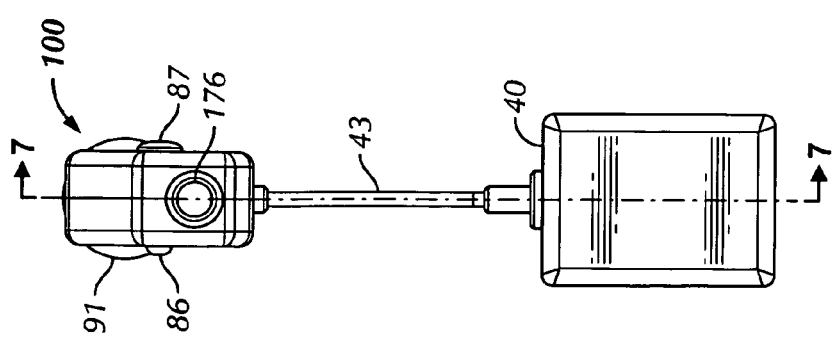
*FIG. 7*
*FIG. 6*

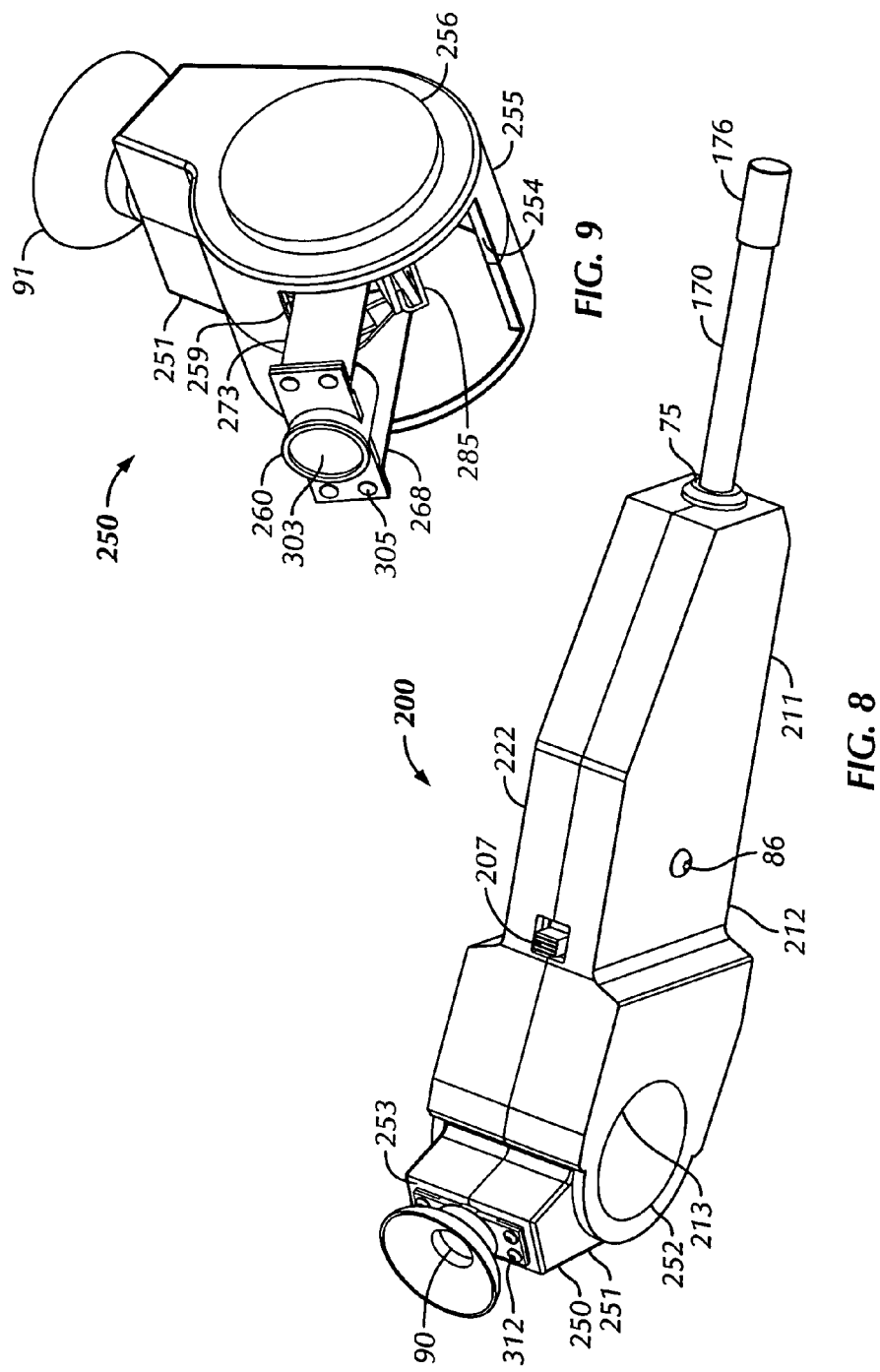

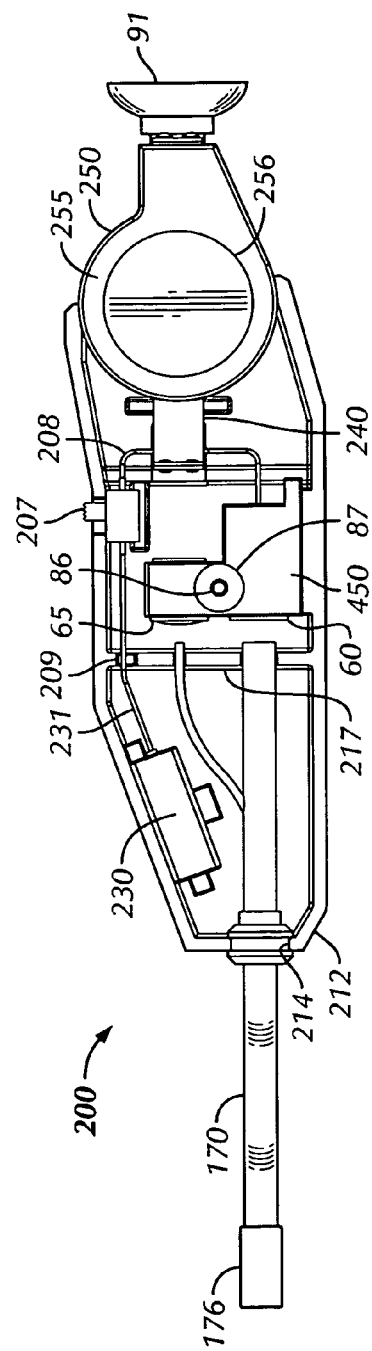
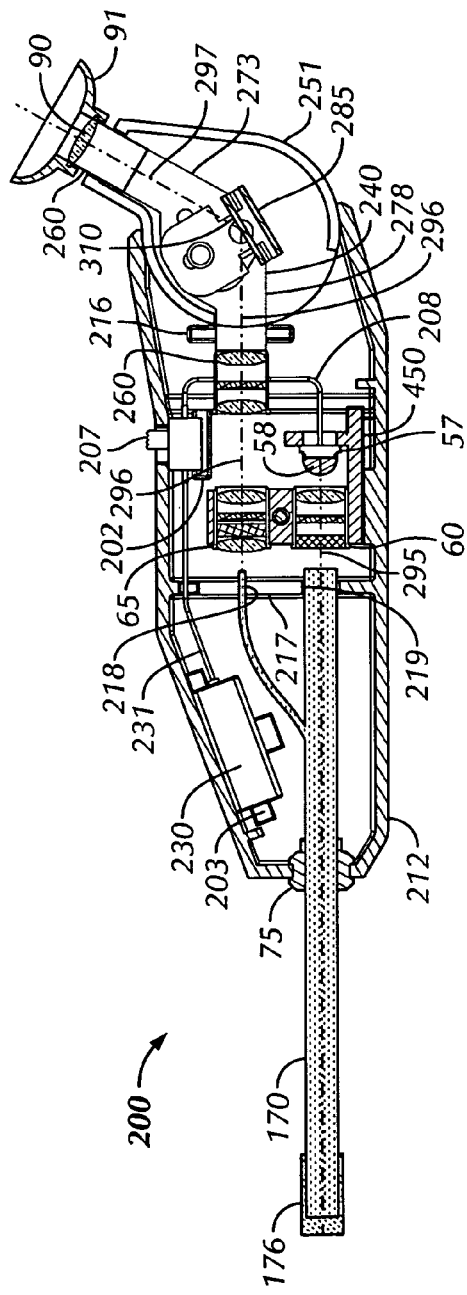

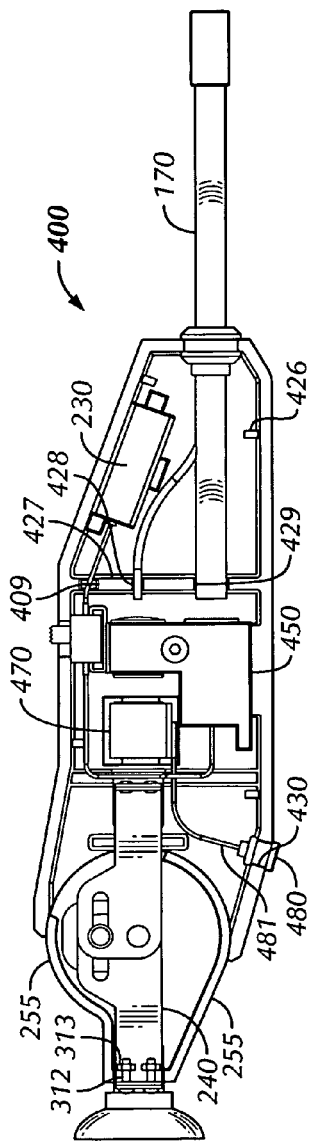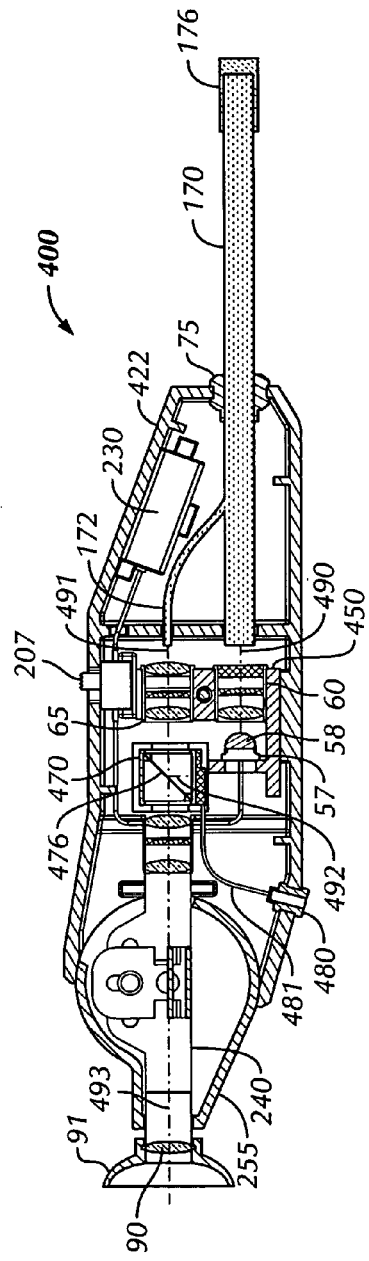

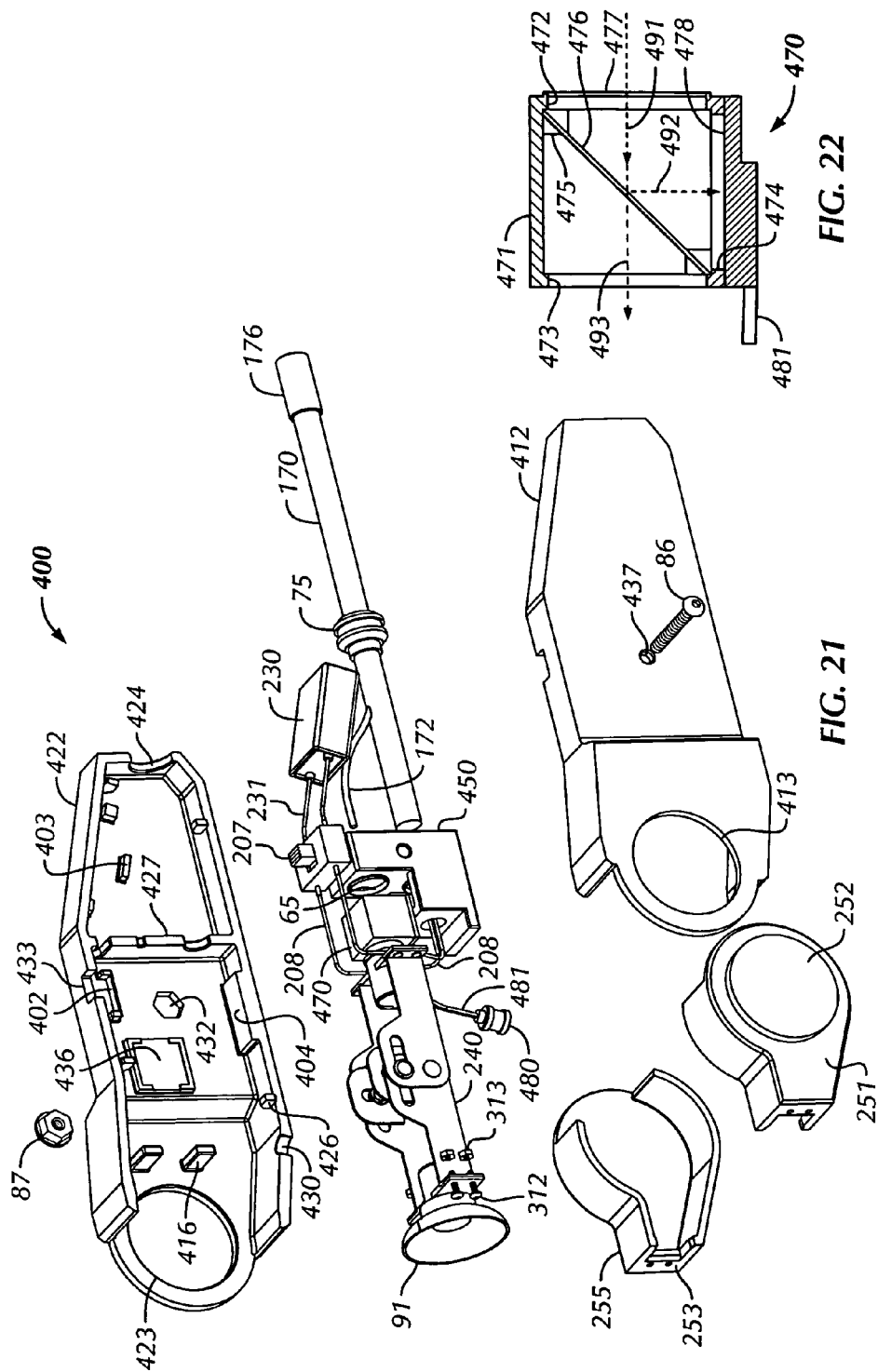

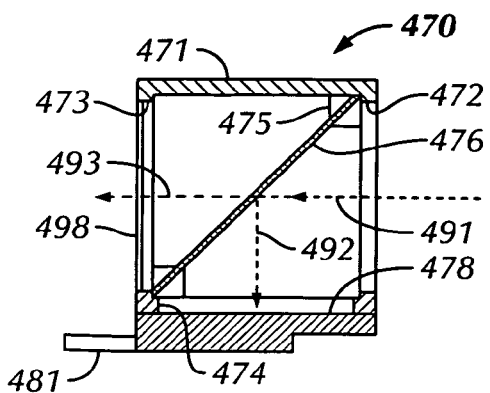
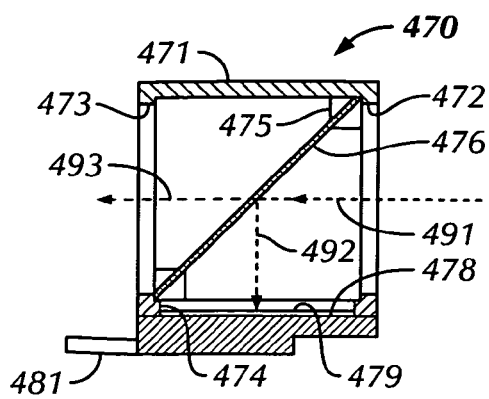
FIG. 23   FIG. 24
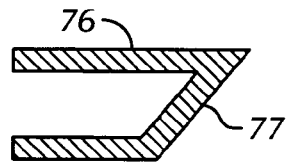
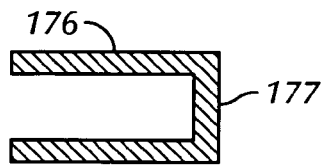
FIG. 25A   FIG. 25C
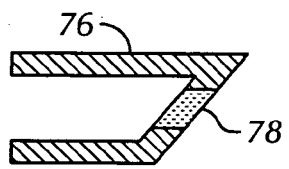
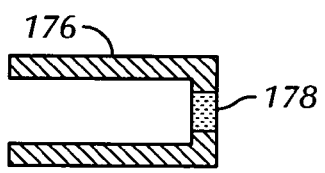
FIG. 25B   FIG. 25D
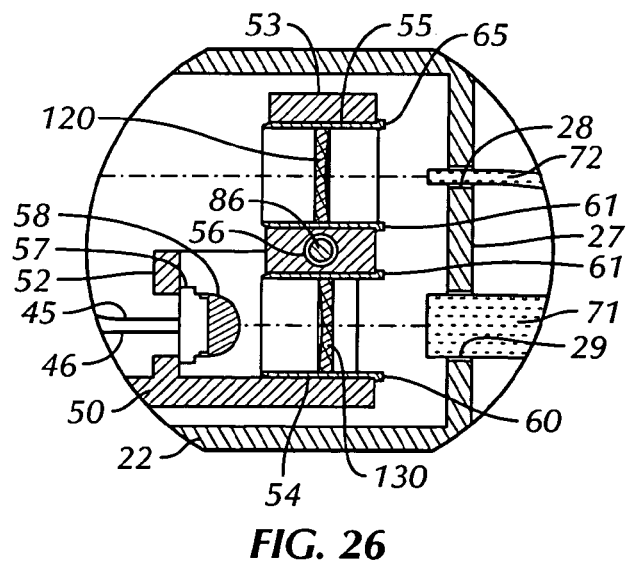
FIG. 26

HANDHELD PORTABLE EXAMINATION DEVICE FOR DIAGNOSTIC USE

CROSS-REFERENCE TO RELATED APPLICATION

The present application, pursuant to 35 U.S.C. 111(b), claims the benefit of the earlier filing date of provisional application Ser. No. 61/063,755 filed Feb. 6, 2008, and entitled "Handheld Portable Microscope for Diagnostic Use."

BACKGROUND OF THE INVENTION

1. Field of the Invention

The present invention relates to a portable apparatus for use in the identification of cancer, in particular the identification of cancer on externally exposed body surfaces.

2. Description of the Related Art

Spectroscopic screening and diagnostic apparatuses have been described that can evaluate tissues at a cellular level. These devices allow for a close-up visual medical examination that can be performed in a doctor's office without having to rely on large sophisticated medical equipment in a hospital or clinical setting. Optically based devices, such as the optical needle biopsy device described in U.S. Publication No. 2007/0173718, are advantageous in providing patient examinations without relocation of the patient to a hospital or clinic and do not require that the patient make a separate appointment time. Furthermore, such devices eliminate or drastically reduce the multiple waiting periods between the examination, removal, and diagnosis of questionable tissue.

One problem with the portable optical spectroscopic screening and diagnostic devices previously described is that the optical probes described are inflexible and difficult to use in examining internal body cavities having limited access.

A need exist for a flexible portable probe having a selectably adjustable angle for the operator to view the tissue being examined.

SUMMARY OF THE INVENTION

The present invention relates to a portable medical examination device used for cancer detection using tissue illumination with radiation of a certain wavelength band to provide the operator with either reflected images of the tissue or by inducing visible fluorescence of the irradiated tissue.

One embodiment of the present invention includes a medical examination device for spectrally screening tissue for cancer having: an illumination source transmitting a light beam through a first lens unit to condition the light beam; a fiber optic bundle including an excitation fiber and an image fiber, wherein the excitation fiber delivers the conditioned light from the first lens unit to a tissue to be examined and wherein the image fiber directs the light emanating from the illuminated tissue to a second lens unit; and an angularly adjustable visualization unit, wherein a light beam conditioned by the second lens unit is visualized by the device operator.

A second embodiment of the present invention includes a medical examination device for the spectral detection of cancer having: an illumination source; a first lens unit conditioning a light beam from the illumination source; an excitation optic fiber delivering the conditioned light beam from the first lens unit to a tissue to be examined; an image optic fiber receiving a light beam emanating from the tissue illuminated with the conditioned light beam and transmitting the emanated light beam through a second lens unit; and a lens support assembly including a first lens holder, a mirror, and an ocular viewer, wherein the first lens holder is held in an aligned position that is coaxially aligned with the second lens unit while the mirror and the ocular viewer are angularly adjustable about the aligned position; whereby the emanating light beam passing through the second lens unit is directed to the mirror and then to the ocular viewer.

Another embodiment of the present invention includes a medical examination device having: an illumination source; a first lens unit conditioning a light beam from the illumination source; an excitation optic fiber delivering the conditioned light beam from the first lens unit to a tissue to be examined; an image optic fiber receiving a light beam emanating from the tissue illuminated with the conditioned light beam and transmitting the emanated light beam through a second lens unit; a beam splitter that splits the emanated light beam from the second lens unit into a first light beam and a second light beam; an image capture device for selectably capturing the first light beam; and a lens support assembly including a first lens holder, a mirror, and an ocular viewer, wherein the first lens holder is held in an aligned position that is coaxially aligned with the second lens unit while the mirror and the ocular viewer are angularly adjustable about the aligned position, and wherein the second light beam is directed to the mirror and then to the ocular viewer.

The foregoing has outlined rather broadly several aspects of the present invention in order that the detailed description of the invention that follows may be better understood and thus is not intended to narrow or limit in any manner the appended claims which define the invention. Additional features and advantages of the invention will be described hereinafter which form the subject of the claims of the invention. It should be appreciated by those skilled in the art that the conception and the specific embodiment disclosed may be readily utilized as a basis for modifying or designing of the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 3 is a longitudinal cross-sectional view of the apparatus of FIG. 2B taken on line 3-3.

FIG. 4 is an enlargement of a portion of FIG. 3, wherein the showing the illumination source and the first and second lens units with mounted filters and lenses.

FIG. 6 is a frontal view of the apparatus of FIG. 5.

FIG. 7 is a longitudinal sectional view of the apparatus of FIG. 6 taken along line 7-7.

FIG. 8 is an oblique lateral view of a third embodiment of the apparatus.

FIG. 9 is an oblique view of the angularly selectably adjustable viewing subassembly for the apparatus of FIG. 8.

FIG. 10 is a profile view from the lefthand side of the apparatus of FIG. 8 with the lefthand housing removed in order to illustrate the arrangement of the interior components of the apparatus with the angularly selectably adjustable viewing subassembly coaxially aligned.

FIG. 11 is a longitudinal sectional view of the apparatus of FIG. 8 taken on the vertical longitudinal midplane with the angularly selectably adjustable viewing subassembly angularly offset.

FIG. 19 is a lateral profile view of the apparatus of FIG. 18 with the righthand housing removed.

FIG. 20 is a longitudinal vertical cross-sectional view of the apparatus of FIG. 18.

FIG. 21 is an oblique exploded view of the apparatus of FIG. 18.

FIG. 22 is a longitudinal sectional view of the beam splitter assembly with a filter mounted on the entry port, wherein the beam splitter permits both electronic imaging and simultaneous direct viewing of the light beam reflected or fluoresced by the sample.

FIG. 23 is a longitudinal sectional view of the beam splitter assembly similar to that of FIG. 22 but with a filter mounted on the exit port.

FIG. 24 is a longitudinal sectional view of the beam splitter assembly similar to that of FIG. 23 but with a filter mounted on the CCD port.

FIG. 25A is a longitudinal sectional view of the disposable sheath for the first embodiment having an angled distal tip.

FIG. 25B is a longitudinal sectional view of the disposable sheath for the first embodiment with an optical coupler incorporated in the distal tip.

FIG. 25C is a longitudinal sectional view of the disposable sheath for the second embodiment having a vertically transverse distal tip.

FIG. 25D is a longitudinal sectional view of the disposable sheath for the second embodiment with an optical coupler incorporated in the distal tip.

FIG. 26 is similar to FIG. 4 showing the illumination source and the first and second lens units with a single filter in each.

DESCRIPTION OF THE PREFERRED EMBODIMENTS

As a note, the use of the terms "invention", "present invention" and variations thereof throughout the subject patent application (and headings therein) are intended to refer or relate to one or more embodiments of the present application, not necessarily every embodiment or claim of the application.

This invention pertains to a compact practical diagnostic apparatus for using portable optical microscopic means to examine biological tissue in situ in a clinical environment. Specifically, the portable examination device of the present invention is used to visually identify cancers or other abnormal cells in a specimen. The cancers which may be identified using the apparatus of the present invention are located on externally exposed, surgically exposed, or accessible interior surfaces of the body of a patient. The configuration of the apparatus may be specifically arranged depending on the anatomical location of potential cancer or user preference.

The portable examination device can be used for cancer diagnosis by using tissue illumination with radiation of a certain wavelength band to provide the operator with either reflected images of the tissue or by inducing visible fluorescence of the irradiated tissue. Use of a contrast agent applied to the tissue can enhance the optical evaluation of tissues.

Figure 1:
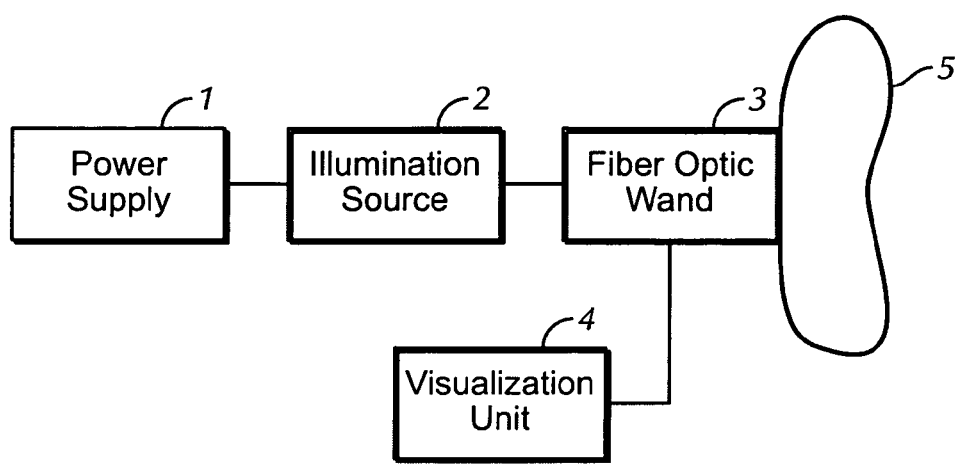
FIG. 1 is a schematic representation of the principle components of the portable examination device.

As illustrated in FIG. 1, the diagnostic apparatus has an illumination source 1, a visualization unit 4, an optical probe or fiber optic wand 3, and a power supply 1. These basic components may be implemented in a variety of embodiments and can be packaged in a number of configurations without departing from the scope of the invention as set forth in the claims.

Four embodiments of the apparatus are shown, with each embodiment arranged to satisfy particular needs. The first embodiment is configured so that the apparatus can be brought adjacent a specimen with the axis of the instrument angularly inclined from the specimen surface.

The second embodiment is similar to the first embodiment, but is configured so that the apparatus is perpendicular to the surface of the specimen. Both the first and second embodiments are powered by external electrical power.

The third embodiment is characterized by internal battery power and an ability to selectably rotate the viewing eyepiece to a more easily viewed position without rotating the entire apparatus.

The fourth embodiment is similar to the third, but is also provided means for electronically capturing images for display on a screen or for electronic storage.

The materials of construction for structural components are typically stainless steel and plastics such as nylon, ABS, fiberglass, and polypropylene. The lenses for the device are generally glass or polycarbonate plastic. A light-emitting diode (LED) is typically used to provide illumination, and insulated copper wiring and connectors are generally used for the transmission of electrical power.

Referring now to the drawings, it is noted that like reference characters designate like or similar parts throughout the drawings. The figures, or drawings, are not intended to be to scale. For example, purely for the sake of greater clarity in the drawings, wall thicknesses and spacings are not dimensioned as they actually exist in the assembled embodiments.

I. Basic Components of the Apparatus

The Illumination Source

One of the basic components of the medical examination device is the illumination source 1. The illumination source includes a lamp and optional lenses and filters.

The lamp is preferably one or more LEDs (light emitting diodes), while other embodiments include an Xenon or Mercury arc lamp, a Helium Cadmium laser, a halogen lamp, and the like. One embodiment of the device uses a plurality of selectable LEDs. Since LEDs are available that emit a variety of colors or emitted wavelength bands, the use of one or more LEDs can be used to provide the desired wavelength band of the light beam emitted.

Although not required, the light from the illumination source is typically conditioned and/or filtered with optical lenses and filters to obtain the desired wavelength band for the light beam used for the medical examination. The light is optionally conditioned or filtered using either one or more selected lenses or filters. If the light beam is to be conditioned using a lens and/or a filter, the lens or filter is positioned between the lamp emitting the light beam and the fiber optic wand that directs the light to the tissue to be illuminate such as in the first lens unit 60.

The first lens unit 60 may have no filter/lens, or it may have any number of filters and/or lenses for conditioning the illumination light beam. Examples of such lenses/filters include, but are not limited to, a polarizing filter, a neutral density filter, a fluorescent filter, and/or a collimating lens. The embodiment illustrated in FIG. 26 utilizes a single filter/lens 130; whereas the embodiment shown in FIGS. 3 and 4 uses both lenses and a conditioning filter to prepare the light used to illuminate the tissue 5.

Fluorescent and/or reflectance spectra are typically used to characterize the pre-cancerous or cancerous condition of the tissue being examined. One or more excitation fluorescence bandwidths may be used, such as 455-465 nm, 410-430 nm, 375-385 nm and/or 340-360 nm, to excite the tissue. Similarly if reflectance is used to examine the tissue, then white light (400-700 nm), or narrower bands such as 455-465 nm, 410-430 nm or 550-590 nm may be used to illuminate the tissue. Parallel and/or cross-polarized light may also be used to enhance different tissue structures.

The Visualization Unit

The visualization unit 4 includes an ocular viewer, optional lenses and filters, an angularly rotatable viewing subassembly, and an optional image capture device, such as an electronic digital camera for displaying, capturing and storing reflectance and/or fluorescence images of the illuminated tissue 5.

The light beam from the illumination source 2 impinges on the tissue to be examined. The light beam emanating from the illuminated tissue sample 5 is optionally filtered or conditioned by a second lens unit 65 before being directed to an ocular viewer and/or a camera for recording.

The second lens unit 65 may have no filter/lens, or it may have any number of filters and/or lenses for conditioning the light beam emanating from the illuminated tissue. Examples of such lenses/filters include, but are not limited to, a polarizing filter, a neutral density filter, a fluorescent filter, and/or a collimating lens. The embodiment illustrated in FIG. 26 utilizes a single filter/lens 120; whereas the embodiment shown in FIGS. 3 and 4 uses both lenses and a conditioning filter to prepare the light used to illuminate the tissue 5. In one embodiment the second lens unit 65 blocks substantially all of the wavelengths in the beam of light selected by the first lens unit 60.

The nature of the emanating light beam will depend on the nature of the impinging light beam. For example, if the impinging light beam is white light, then the returning light beam is reflected light. Alternatively, if the light beam is fluorescent light that impinges on the surface of the tissue 5 causing it to fluoresce, then the returning light beam will be the resultant fluorescence from the tissue 5.

The embodiment of the visualization unit 2 illustrated in FIGS. 8-11 includes an operator angularly adjustable viewing subassembly 250. The light beam emanating from the illuminated tissue 5 is directed through the second lens unit 65 to a mirror 310 mounted in a lens support assembly 240 which allows the light beam impinging on the mirror 310 to be directed to the ocular viewer 90 when the viewing lens 90 has been adjusted to a variety of angles from the axis of the image receiving fiber or the second lens unit.

The lens support assembly includes a first lens holder, a mirror, and an ocular viewer. The first lens holder is held in a position that is coaxially aligned with the image receiving fiber or the second lens unit while the mirror and the ocular viewer are angularly adjustable. The ocular viewer is angularly adjustable up to a 90° angle from the axis of the second lens unit.

The embodiment of the visualization unit 2 illustrated in FIGS. 20-22 includes an image capture device, such as a CCD imaging device. The fluorescence or reflected light from the tissue 5 is returned in a beam 491 to the visualization unit 2. This embodiment of the visualization unit 2 passes the light beam 491 through a beam splitter assembly 470. Examples of a beam splitter include without limitation a dichroic mirror, a half silvered mirror, or a polarization beam splitter. The beam splitter assembly 470 allows the tissue image to be visually seen by the operator through the ocular device while a reflected image is available to be photographed or captured by the CCD imaging device.

The Fiber Optic Wand

The fiber optic wand or optical probe 3 provides a microscopic view of a specific site on the tissue 5. The fiber optic wand 3 is a contacting optical probe that delivers a light beam to the tissue 5 via an array of multiple fiber optic excitation strands or fibers and collects the emanated light from the tissue with one or more fiber optic collection strands or fibers. Preferably, multiple collection or image fibers are used, where the image fibers are in a coherent bundle. A coherent bundle of image fibers have the same spatial organization at the both its proximal and distal ends. Throughout the description herein the term "image fiber" refers to a coherent bundle of image fibers.

Figure 5:
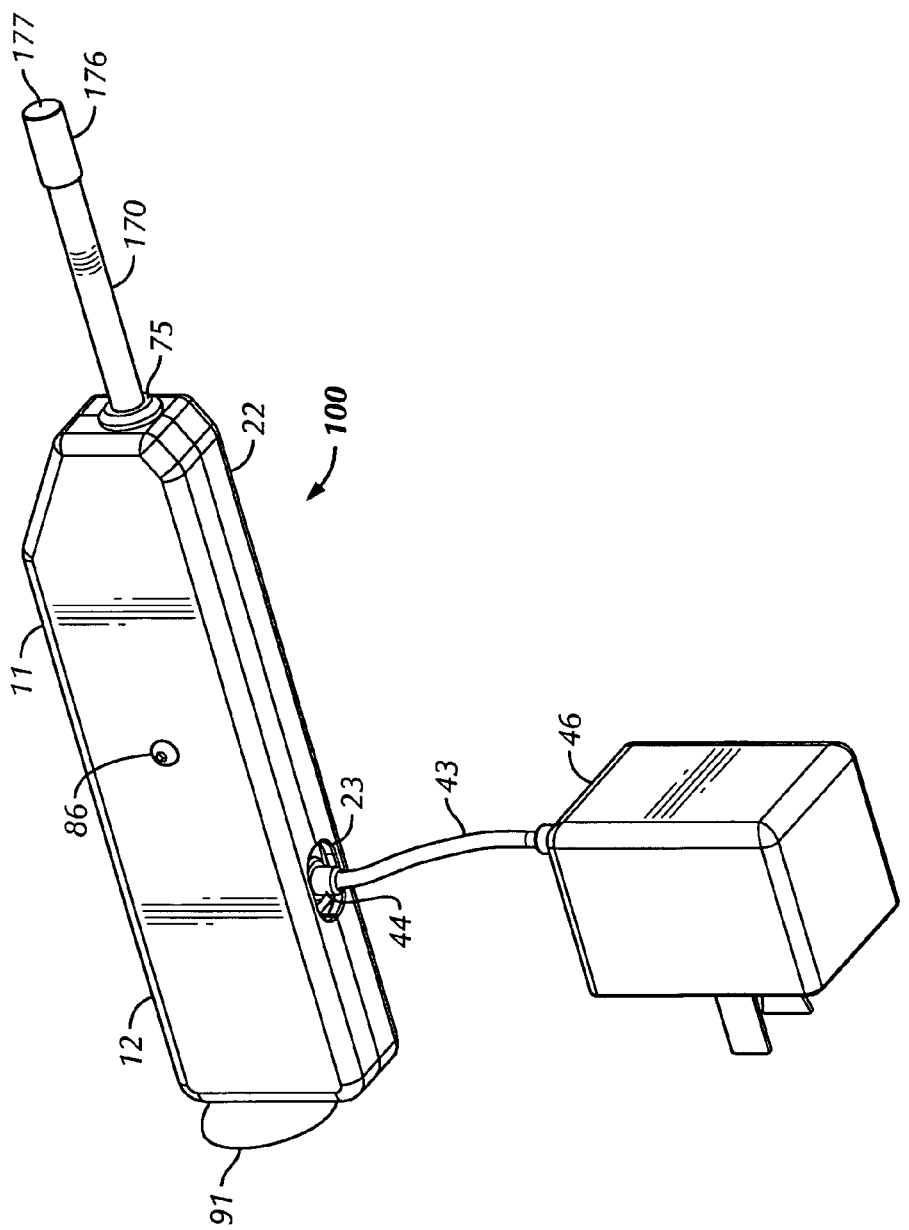
FIG. 5 is an oblique side view of a second embodiment of the apparatus.

One embodiment of the fiber optic wand or optical probe 3 described herein is shown in FIGS. 5, 7, and 8. The probe has a shaft with a distal end for placing on a tissue site 5 to be examined. The probe shaft extends from the distal end of the portable examination device housing. A continuous bi-directional fiber optic bundle 171 runs through the probe shaft to the distal end of the shaft. The fiber optic assembly 70 or 170 may be constructed with any number of excitation fibers and collection fibers in a variety of configurations. For example, the excitation fibers may be located around the periphery of the image fiber bundle.

The fiber optic wand or optical probe 3 has an optional disposable sheath 76 or 176 for isolating the distal end of the shaft and/or the fiber optic bundle from the tissue sample, when the portable examination device is to be used in the clinic. The distal tip 77 or 177 of the sheath is used to contact the tissue specimen of interest.

The distal tip 77 or 177 of the disposable sheath may have an optical coupler or lens for optically conditioning the light. FIG. 25B illustrates an optical coupler 78 in the distal tip 77 of the sheath 76, whereas FIG. 25D illustrates an optical coupler 178 in the distal tip 177 of the sheath 176. When the optical conditioning assembly or optical coupler 78 or 178 is present at the distal tip of the sheath, the optical coupler contacts the tissue specimen of interest.

The sheath 76 or 176 and/or its distal tip 77 or 177 is constructed of a material that is non- or minimally light scattering and transparent to the emitted wavelength band of light used for the spectrographic investigation and any reflected or fluorescent light passing back into the wand from the tissue 5. In addition, the material should generate minimal autofluorescence.

It should be noted here that when the disposable sheath 176 is positioned on the fiber optic wand 3 that it is considered a part of the probe and the distal end 177 of the sheath 176 becomes the distal end of the probe 3.

The Power Supply

The power supply 1 for the medical examination device may either be a rechargeable battery pack or supplied through an electrical cord. FIG. 1 shows one embodiment of the power supply 1 and its interaction with the illumination source of the portable examination device. The power supply 1 may also be used to power an image capture device such as a charge-coupled device (CCD) so that the image can be stored, enlarged, viewed and/or spectrally analyzed on a separate external device such as a viewer or computer.

The power supply 1 regulates output voltages and currents for the illumination source 2 and/or the image capture device.

II. First Embodiment of the Apparatus

Figure 2A:
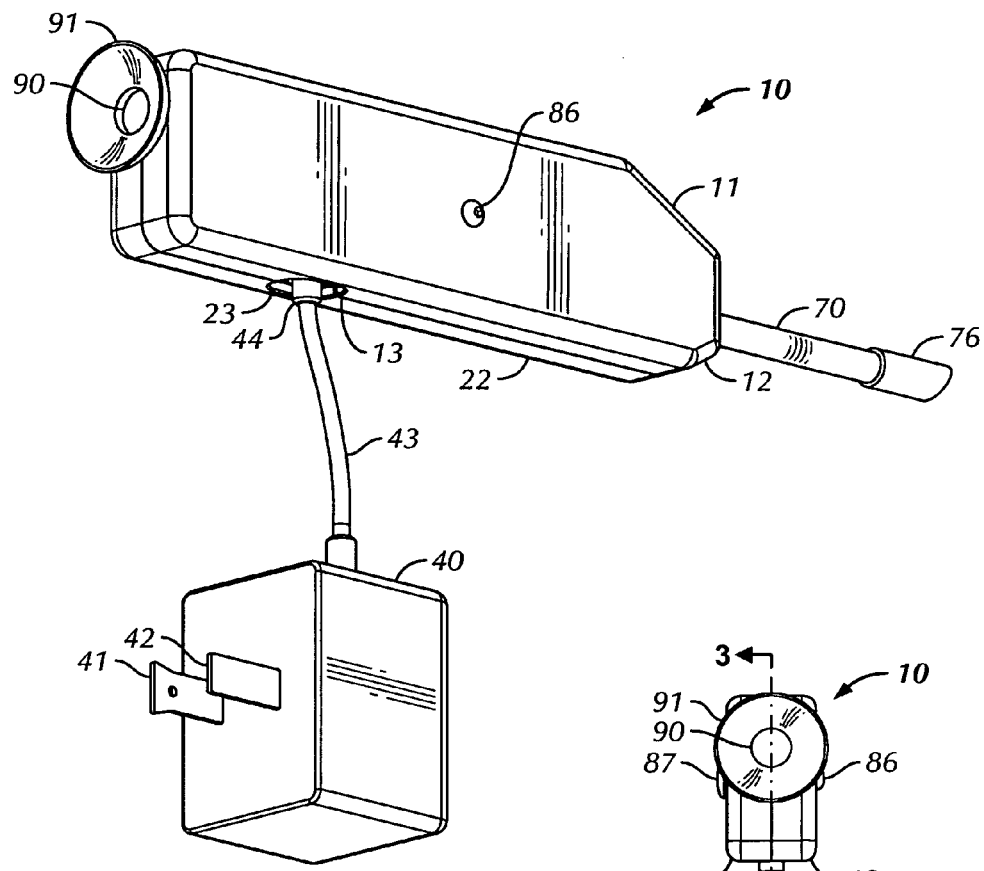
FIG. 2A is an oblique rear view of the first embodiment of the invention.
Figure 2B:
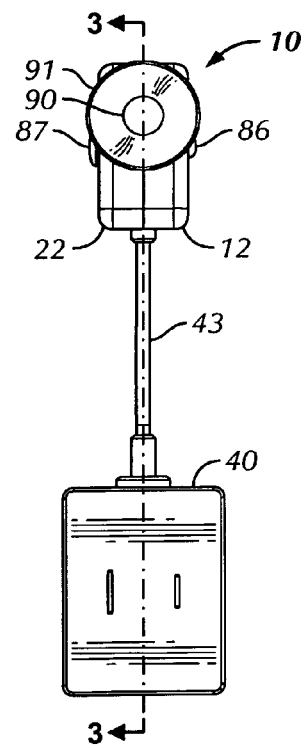
FIG. 2B is a rear view of the apparatus of FIG. 1.

FIGS. 2 to 4 illustrates the first embodiment 10 of the portable examination device in an oblique rear view, a rear view, a longitudinal cross-sectional view, and a detail view, respectively.

The primary components of the first embodiment portable examination device 10 consists of a housing 11, a power supply 40, an illumination source or LED 57, a fiber optic wand assembly 70, lenses and optical filters in a lens mounting block 50, and an ocular viewing device or lens 90. The housing 11 is made of righthand and lefthand molded plastic housing halves 12 and 22, respectively. Except as noted, the two housing halves 12 and 22 are mirror-image parts which surround the internal components of the apparatus 10.

Details of the lefthand housing half 22 are shown in FIGS. 3 and 4. The lefthand housing half is a thin wall body with a vertical outer wall offset from the midplane of the housing assembly and a perpendicular peripheral wall extending normal to the midplane of the housing assembly 11. Housing half 22 has a vertical planar mating face comatable with a corresponding face for righthand housing half 12 at the midplane of the housing assembly. The perpendicular peripheral wall of housing half 22 has a horizontally elongated perimeter wall having a rear vertical transverse end, an intermediate vertical transverse diaphragm 27, a vertical transverse forward end, and parallel upper and lower sides. The height of the lefthand housing half 22 is reduced at its forward end by inclined flat transition sections. Offset from the mating face of the lefthand housing half 22 is a flat outer wall connected to the perpendicular peripheral wall. The distance between the mating face and the outer wall is less than the height of the lefthand housing half.

On the lower side of both housing halves 12 and 22 are located semicircular cutouts 13 and 23, respectively, which serve as power cord openings. As seen in FIG. 3, lefthand housing half 22 has a semicircular cutout wand opening 24 on its forward vertical end which mounts an elastomeric grommet 75 which serves to centralize the fiber optic wand 70 where it passes out of the housing 11. On the rear vertical end of the housing half 22 is located a semicircular cutout view port opening 25 for mounting an ocular eyepiece lens 90 and an elastomeric eye cup 91 on the midplane of the housing 11. All of the semicircular cutouts 13, 23, 24, and 25 have the axes of the semicircles on the mating plane of the housing halves 12 and 22.

The lefthand housing half 22 has on the inner side of its peripheral wall multiple alignment bosses 26 which extend horizontally past the vertical mating face of the housing half but which do not extend beyond the inner side of the peripheral wall in an outward direction. These alignment bosses 26 serve to maintain alignment between the two housing halves 12 and 22. Alignment bosses 26 represent the only departure from mirror imagery for the two housing halves 12 and 22.

The vertical transverse bulkhead 27 of housing half 22 is provided with horizontal axis semicircular cutouts 28 and 29 which have their axes on the mating plane of the housing half. Cutout 28 serves as a locator and passageway for the image fiber bundle 72 and cutout 29 serves the same purpose for the main fiber bundle 71 of the fiber optic assembly 70.

Corresponding coaxial horizontal holes penetrate the vertical outer walls of both the righthand 12 and lefthand 22 housing halves. These coaxial holes permit the housing screw 86 to extend through both holes and to there engage housing nut 87 so that the housing halves can be assembled into alignment and clamped together.

The power supply 40 for the first embodiment 10 consists of a rectangular prismatic block having first 41 and second 42 parallel but laterally offset power prongs projecting normally from one side. The power prongs 41 and 42 are configured for connective engagement into a standard 120 volt AC wall socket. The power supply block contains conversion means for rectifying and stepping down the AC wall plug voltage to a DC current suitable for the operation of the illumination source. Power cord 43 containing a first power conductor 45 and a second power conductor 46 connects the power supply 40 and the illumination source. The illumination source 2 is preferably one or more LEDs (light emitting diodes), although other embodiments include a Xenon or Mercury arc lamp, a Helium Cadmium laser, or a halogen lamp. The illumination source shown in FIG. 3 is typically an LED light source 57. Grommet 44, mounted on power cord 43, serves to support the power cord and limit it's bending where it is engaged with the lens mounting block 50, as seen in FIG. 3.

Lens mounting block 50 is typically either a metallic or molded plastic body symmetric about its vertical midplane, which is located on the mating plane of the housing halves 12 and 22. The external surface of lens mounting block 50 is composed of rectangular prismatic elements. From the rear end, lens mounting block 50 has a vertically thin flat element projecting forward to support an upwardly extending lower block which in turn mounts another upwardly extending but longitudinally shorter upper block 53. The front vertical faces of the lower and upper 53 upwardly extending blocks are flush. On the centerline of the horizontal thin flat element of the lens mounting block 50 is a vertically extending hole which serves as a power cord opening 51 for supporting grommet 44 of the power cord 43.

An upwardly opening rectangular cavity extends into the upper face of the lower upwardly extending block to the level of the upper surface of the thin flat element of the block, thereby creating vertical transverse bulkhead 52 on the rear face of the lower upwardly extending block. The forward vertical face of the upwardly opening cavity is flush with the rear face of the upper block 53. The transverse bulkhead 52 is penetrated by a small horizontal axis hole which is coaxial with a larger first lens mounting bore 54. The hole in the transverse bulkhead 52 provides a passage for the first 45 and second 46 conductors of the power cord 43.

The first lens mounting bore 54 extends forward from the forward side of the upwardly opening cavity to penetrate the lower upwardly extending block. A similar second lens mounting bore 55 is vertically offset to penetrate the upper block 53. A transverse retention screw hole 56 penetrates the lens mounting block 50 between the first 54 and second 55 lens mounting bores.

A LED light source 57 having integral lens 58 is mounted on the forward side of the transverse bulkhead 52 concentric with the first lens mounting bore 54 of the lens mounting block 50. The first conductor 45 and the second conductor 46 of the power cord 43 are attached to the rear face of the LED 57 to power the LED.

A first lens unit 60 is mounted in the first mounting bore. The first lens unit 60 includes a lens mounting tube 61 and an optional number of lenses and/or filters to condition the light from the LED 57. The first lens unit 60 may only contain a neutral density filter, so that it does not affect the light beam 81 passing through it. However, it is more common for the lens unit 60 to contain one or more filters and/or lenses as illustrated in FIG. 26 and FIG. 4. One example of the first lens unit 60, shown in FIG. 4, includes a first lens 62, a second lens 63, and an optical filter 64.

The lens mounting tube 61 is a horizontal axis thin wall tube which has an outwardly projecting flange on its forward end. The outer cylindrical surface of the tube 61 is a close fit to the first lens mounting bore 54 of the lens mounting block 50. The first lens 62, the second lens 63 and the filter 64 all have the same outer diameter which is a close fit to the bore of the tube 61 in which they are mounted. From the rear and extending in the forward direction, the mounting of components in the mounting tube 61 is the first lens 62, the second lens 63, and then the filter 64.

The second lens unit 65 is similar to the first lens unit 60 and includes a lens mounting tube 61 and any number of filters and/or lenses desired. Although the second lens unit may only contain a neutral density filter, it will more likely contain at least one lens and/or filter. For example the second lens unit 65 illustrated in FIG. 4 includes a first lens 66, a second lens 67, an optical filter 68, and a third lens 69.

The outer cylindrical surface of the tube 61 is a close fit to the second lens mounting bore 55 of the lens mounting block 50. Lenses 66, 67, 69, and filter 68 all have the same outer diameter which is a close fit to the bore of the tube 61 in which they are mounted. From the rear and extending in the forward direction, the mounting of components in the mounting tube 61 of second lens unit 65 is the first lens 66, the second lens 67, the filter 68, and then the lens 69. Both the first 60 and second 65 lens units are inserted into their respective mounting bores 54 and 55 until their mounting tube flanges are flush with the forward vertical face of the lens mounting block 50.

The fiber optic assembly 70 of the first embodiment consists of a shaft and a straight cylindrical main fiber optic bundle 71 having a number of individual excitation fibers and at least one image receiving fiber 72. The image receiving fiber 72 is typically a coherent fiber bundle that exits the main fiber optic bundle 71 and is vertically offset from the axis of the main bundle at its rearward end.

At its forward end the image receiving fiber 72 is bent to enter the main fiber optic bundle 71 and is typically placed in a central position within the main fiber optic bundle 71 at its forward end. The diameter of the image receiving fiber 72 is often larger than the excitation fibers in the main bundle 71. The distal (forward) end of the main bundle 71 with its centrally located image receiving fiber 72 has a planar cut symmetrical about the vertical midplane so that its lower fibers are shorter than its upper fibers. This angular probe and image receiving fiber or fiber bundle 72 is advantageous in that any specular reflection from the interface is directed away from the collector path and the image fiber bundle 72. Such specular reflection is caused by an imperfect contact between the tissue and the distal end of the probe or sheath due to an uneven tissue surface, as well as a difference in the index of reflectance between the tissue and the distal tip of the probe/sheath.

A grommet 75 is deployed around the shaft of the fiber optic assembly 70 on the forward side of the junction of the image receiving fiber 72 and the main fiber optic bundle 71. The engagement of the grommet 75 with the semicircular wand opening 24 and the engagement of the main bundle 71 with the main fiber opening 29 of the lefthand housing half 22 locates and aligns the fiber optic assembly 70 relative to the housing 11. Additionally, the close fit of the image receiving fiber 72 with the semicircular image fiber opening 28 of the housing half 22 aligns and stabilizes that fiber relative to the housing 11. Although not shown herein, the corresponding cutouts in the antisymmetric righthand housing half 12 serve to perform the same alignment and positioning functions as the cutouts of the lefthand housing half 22.

When in clinical use, a close fitting transparent disposable plastic sanitary sheath 76 having a thin distal end is interposed over distal end of the shaft of the fiber optic assembly 70 for sanitary reasons. The closed outer end of the sanitary sheath 76 has a uniform thickness planar face having the same angular orientation as that of the distal tip of the main fiber optic bundle 71.

The distal tip 77 of the sanitary sheath 76 is used to contact the tissue 5 to be examined. The distal tip may have a lens/filter or optical coupler 78 inset in the distal tip 77 of the sheath 76. The plastic of the disposable sanitary sheath 76 is selected so that it is transparent to both the emitted wavelength band of light used for the illumination of the specimen and any reflected or fluoresced light coming from the irradiated specimen.

An eyepiece ocular lens 90 and an elastomeric eye cup 91 are mounted at the rear transverse face of the housing 11 by means of their engagement with the semicircular cutout view port opening 25 in the lefthand housing half 22. As before, the corresponding cutout in the antisymmetric righthand housing half 12 coacts with the opening 25 to centralize the lens 90 and eye cup 91 so that they are coaxial with the exposed interior end of the image receiving fiber 72 of the fiber optic assembly 70.

III. Second Embodiment of the Apparatus

A second embodiment 100 of the portable examination device is seen in use in an oblique side view in FIG. 5, a frontal view in FIG. 6, and a longitudinal sectional view in FIG. 7. The second embodiment portable examination device 100 primarily consists of a housing 11, a power supply 40, an illumination source such as the laser light source 157, a fiber optic wand assembly 170, lenses and optical filters in a lens mounting block 50, and an ocular viewer 90.

As with the first embodiment 10, the housing 11 is made of righthand and lefthand molded plastic housing halves 12 and 22, respectively. Except as noted previously, the two housing halves 12 and 22 are mirror-image parts which surround the internal components of the apparatus 100. Furthermore, the mounting of the components of the second embodiment 100 is the same as for the first embodiment 10.

The fiber optic assembly 170 is substantially similar to fiber optic assembly 70 of the first apparatus embodiment 10, with the exception that the forward end of the fiber optic bundle 171 has a transverse cut so that the end is vertical. To accommodate this change, the forward end of the sanitary sheath 176 is perpendicular to the axis of the sheath, so that the specimen contact surface 177 is perpendicular.

Accordingly, the second portable examination device embodiment 100 is functionally and structurally substantially similar to the first embodiment 10, with the exception of a transverse distal end of the main fiber optic bundle 171 and the image fiber 172.

IV. Third Embodiment of the Apparatus

The third embodiment portable examination device 200 is shown in an oblique view in FIG. 8, a left side profile view with the lefthand housing half 222 removed in FIG. 10, and in a longitudinal sectional view in FIG. 11. FIGS. 9 through 17 show details of a mechanism included in the third embodiment to permit the user of the examination device 200 to change the orientation of the user viewing axis relative to the axis of the fiber optic assembly 170.

The third embodiment portable examination device 200 primarily consists of a housing 211, a battery power source 230 with an operator selectable on-off switch 207, a light-emitting diode (LED) light source 57, a fiber optic wand assembly 170, lenses and optical filters in a lens mounting block 450, and a selectably angularly adjustable rotatable viewing subassembly 250.

With the exception of the use of battery power and modifications enabling provision of the rotatable viewing subassembly 250, the third embodiment portable examination device 200 is functionally and structurally similar to the second embodiment 100. The third embodiment 200 of the portable examination device uses many of the similar components as does the second embodiment 100. As with the first and second embodiments 10 and 100, the housing 211 is made of righthand and lefthand molded plastic housing halves 212 and 222, respectively. Except as noted below, the two housing halves 212 and 222 are mirror-image parts which surround the internal components of the apparatus 200.

Details of the righthand housing half 212 are shown in FIGS. 10 and 11. The righthand housing half 212 is a thin wall body with a vertical outer wall offset from the midplane of the housing assembly and a perpendicular peripheral wall extending normal to the midplane of the housing assembly 211. Housing half 212 has a vertical planar mating face comatable with a corresponding face for lefthand housing half 222 at the midplane of the housing assembly. The perpendicular peripheral wall of housing half 212 has a horizontally elongated upper and lower perimeter walls having a rear opening, an intermediate vertical transverse diaphragm 217, and a vertical transverse forward end.

The height of the righthand housing half 212 is reduced at its forward end by inclined flat transition sections, with the upper flat transition section extending approximately 40% of the length of the housing half. In the midsection of the righthand housing half 212, the upper and lower peripheral wall surfaces are parallel and horizontal. At its rear end, the upper and lower peripheral wall surfaces are also parallel, but are inclined upwardly towards the rear.

Offset from the mating face of the righthand housing half 212 on its forward section is a flat outer wall connected to the perpendicular peripheral wall. The distance between the mating face and the outer wall is less than the height of the righthand housing half. As can be seen best in FIG. 8, the righthand housing half 212 is widened toward the rear from the junction of the horizontal portion to the rearwardly upwardly inclined portion of the upper and lower peripheral walls.

The rearward section of the housing 211, consisting of about one third of its length, has a vertical outer wall which is parallel to but offset more from the vertical housing midplane than the forward end of the housing. The rearward section of the vertical outer wall is arcuate with the axis of the arc horizontal and perpendicular to the midplane of the housing. Coaxial with the axis of the arc on the rearward section of the vertical outer wall is a transverse circular guide bore opening 213. The rearmost section of the vertical outer wall extends farther to the rear than do the upper and lower peripheral walls of the righthand housing half 212.

As seen in FIGS. 10 and 11, righthand housing half 212 has a semicircular cutout wand opening 214 on its forward vertical end which mounts an elastomeric grommet 75 which serves to centralize the fiber optic wand 170 where it passes out of the housing 211. On the upper horizontal side of the housing half 212 is located a rectangular cutout for accommodating the on/off switch 207 for the electric power.

Although not shown herein, the lefthand housing half 222 can have on the inner side of its peripheral walls multiple alignment bosses which extend horizontally past the vertical mating face of the housing half but which do not extend beyond the inner side of the peripheral wall in an outward direction. These alignment bosses can serve to maintain alignment between the two housing halves 212 and 222. Any alignment bosses would represent the only departure from mirror imagery for the two housing halves 212 and 222.

The vertical transverse bulkhead 217 of housing half 212 is provided with horizontal axis semicircular cutouts 209, 218, and 219 which have their axes on the mating plane of the housing half. Cutout 218 serves as a locator and passageway for the image fiber 172 and cutout 219 serves the same purpose for the main fiber bundle 171 of the fiber optic assembly 170. Cutout 209 serves as a passage for one or more battery cables 231. All of the semicircular cutouts 214, 209, 218 and 219 have the axes of the semicircles on the mating plane of the housing halves 212 and 222.

Bosses are provided on the interior vertical faces of the flat outer wall to locate internal components housed within the housing 211. For righthand housing half 212, inwardly projecting boss 202 locates switch 207, multiple bosses 203 locate the battery 230, and a low height boss 204 extends inwardly above the interior horizontal lower wall of housing 212 to locate the lens mounting block 450. Additionally, two restraining bosses 216 project from the interior vertical wall towards the housing midplane symmetrically positioned about a horizontal plane passing through the axis of guide bore opening 213. The bosses 216 closely fit around the upper and lower edges of the first righthand link 262 of the lens support assembly 240 of the rotatable viewing subassembly 250, thereby locating that assembly. The corresponding bosses of the lefthand housing half 222 likewise closely engage the upper and lower edges of the first lefthand link 278 of the lens support assembly 240 of the rotatable viewing subassembly 250.

Corresponding coaxial horizontal holes penetrate the vertical outer walls of both the righthand 212 and lefthand 222 housing halves. These coaxial holes permit the housing screw 86 to extend through both holes and to there engage housing nut 87 so that the housing halves can be assembled into alignment and clamped together.

The battery 230 is a rectangular prism which has terminals on its rear face. Battery cables 231 are connected to the battery on their first ends and to the switch 207 on their second ends. Switch 207 is a double throw two-position slide switch with its switch handle projecting upwardly through rectangular notches in the housing halves 212 and 222. LED power cables 208 extend from the switch 207 to the LED 57. The battery 230 is located within the housing 211 by the multiple bosses 203 of the righthand housing half 212 and the corresponding bosses on the mirror-image lefthand housing half 222.

The lens mounting block 450 for the third embodiment 200 is substantially similar to the lens mounting block 50 used for the first two embodiments 10 and 100, with the exception of the shortening of the rearwardly projecting vertically thin element and the elimination of the power cord opening 51.

The lens mounting block 450, like the lens mounting block 50, mounts the LED 57 with its integral lens 58 and the first lens unit 60 and the second lens unit 65. The lens mounting block 450 is supported and located on its lower side by the boss 204 and is further restrained by the passage of clamping screw 86 through its central transverse hole.

The fiber optic assembly 170, the grommet 75, and the sanitary sheath 176 of the second embodiment 100 are all used with the third embodiment 200 and are located in the same manner as in the second embodiment, with restraint and location being provided by the wand opening 214, the image fiber opening 218, and the main fiber optic bundle opening 219 of the righthand housing half 212 and the corresponding openings of the lefthand housing half 222.

Referring to FIG. 9, the rotatable viewing assembly 250 of the third embodiment 200 is seen in an oblique view from its forward lower left side. The rotatable viewing subassembly 250 is housed within mirror-image righthand 251 and lefthand 255 covers. For ease of description, only the lefthand cover 255 is described herein.

As seen in FIG. 10, the cover 255 is a thin wall plastic or metal structure having, when seen from the outside looking normal to the vertical midplane of symmetry, a planar outer face with a circularly arcuate rounded forward end and a low height round boss 256 concentric with the arcuate forward end. The round boss 256, corresponding to the round boss 252 in the righthand housing half 212, is a slip fit to the guide bore opening in the lefthand housing half 222 corresponding to the opening 213 in the righthand housing half 212.

On the rear side, the planar outer face has a radially protruding extension having a vertical rearward side perpendicular to and symmetrical about a horizontal radius emanating from the center axis of the arcuate forward end. The radially protruding extension has a horizontal top edge, while its lower edge is tangent to the arcuate forward end.

A peripheral end wall extends between the planar outer face of cover 255 and the mating vertical midplane of the righthand 251 and lefthand 255 covers. As seen in FIG. 9, the peripheral end wall is not continuous, but has a cutout extending from slightly below the horizontal midplane to considerably above the horizontal midplane. The horizontal lower edge 254 of the cutout is positioned to just clear the lower side of the lens support assembly 240 when the rotatable viewing assembly 250 is straight, while the horizontal upper edge 259 of the cutout is positioned to just clear the upper side of the lens support assembly when the rotatable viewing assembly is at its maximum rotation position. The latter case is seen in FIG. 9.

The transverse end face 253 of the lefthand cover 255 is provided with a rectangular cutout having its axis on both the mating midplane and the axis of the arcuate rounded forward end of the lefthand cover 255. The cutout accommodates a lens housing 260 of the lens support assembly 240. Mounting screw holes are provided in the transverse end face 253 for the attachment of the flange 261 of a lens housing 260.

Figure 12:
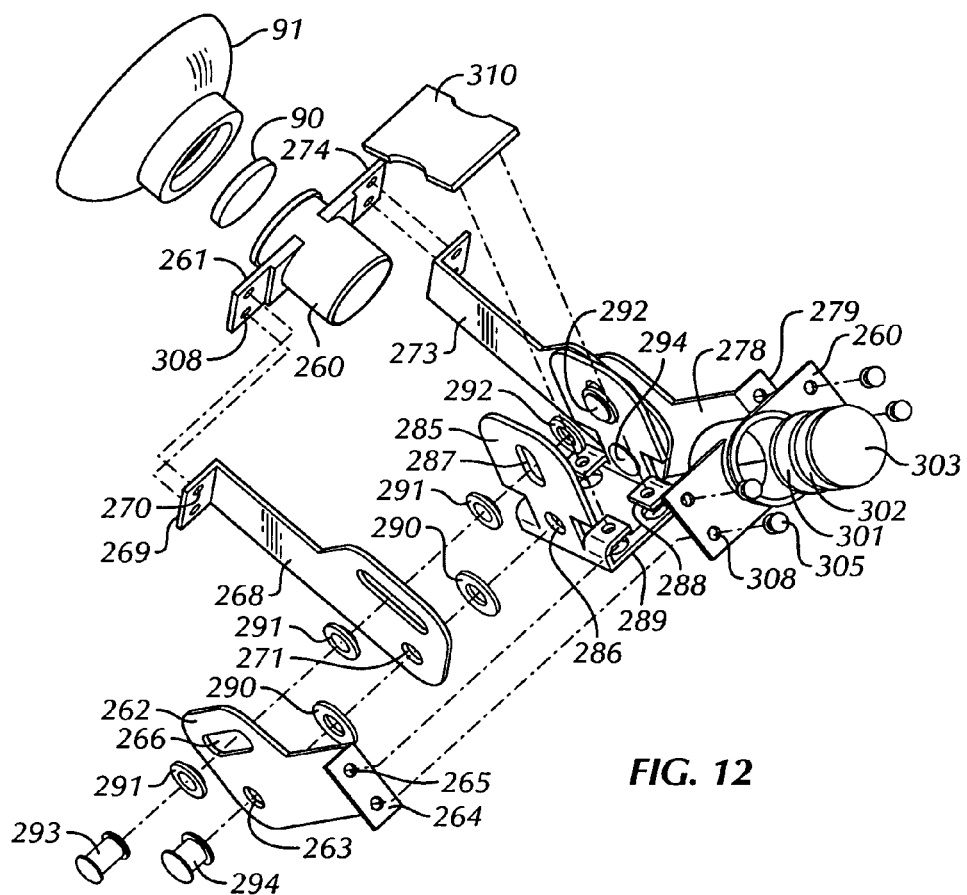
FIG. 12 is an exploded oblique view of the angularly selectably adjustable subassembly of the third embodiment apparatus of FIG. 8.
Figure 13:
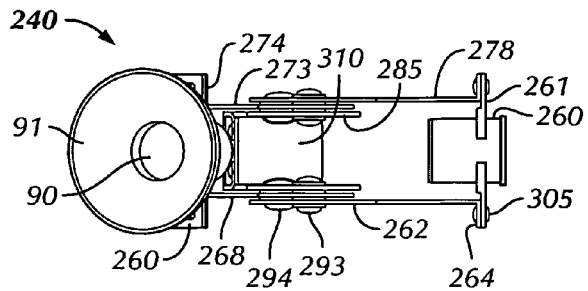
FIG. 13 is a plan view of the unexploded angularly selectably adjustable subassembly of FIG. 12, wherein the subassembly is angularly offset.
Figure 14:
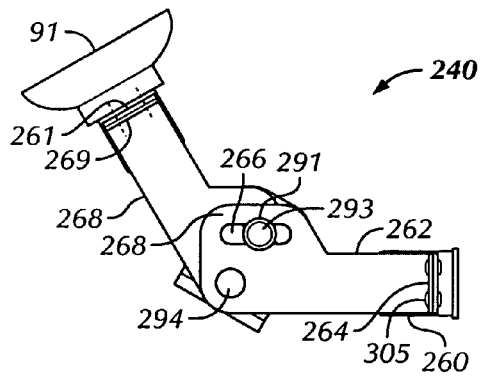
FIG. 14 is a side profile view of the angularly selectably adjustable subassembly of FIG. 13.
Figure 15:
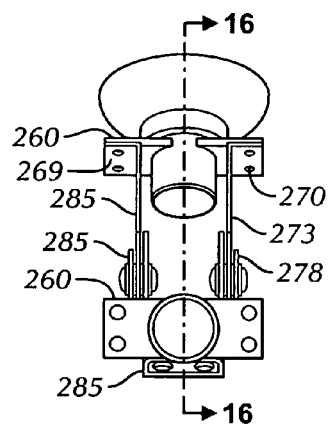
FIG. 15 is a front profile view of the angularly selectably adjustable subassembly of FIGS. 13.
Figure 17:
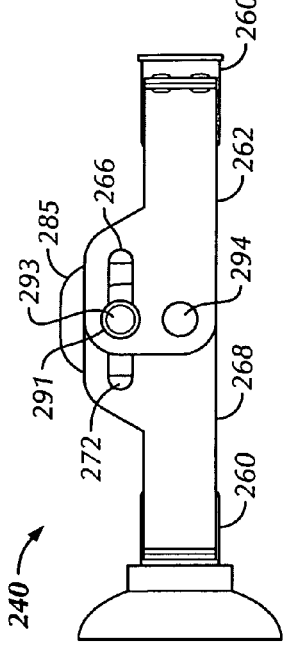
FIG. 17 is a side profile view of the angularly selectably adjustable subassembly with the subassembly coaxially aligned, rather than angularly offset.
Figure 16:
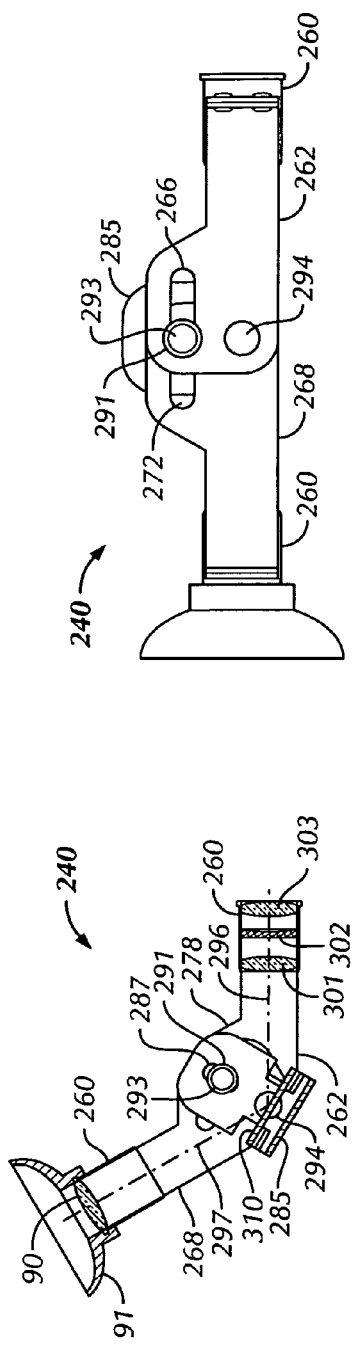
FIG. 16 is a longitudinal vertical cross-sectional view of the angularly selectably adjustable subassembly of FIG. 13.
Figure 18:
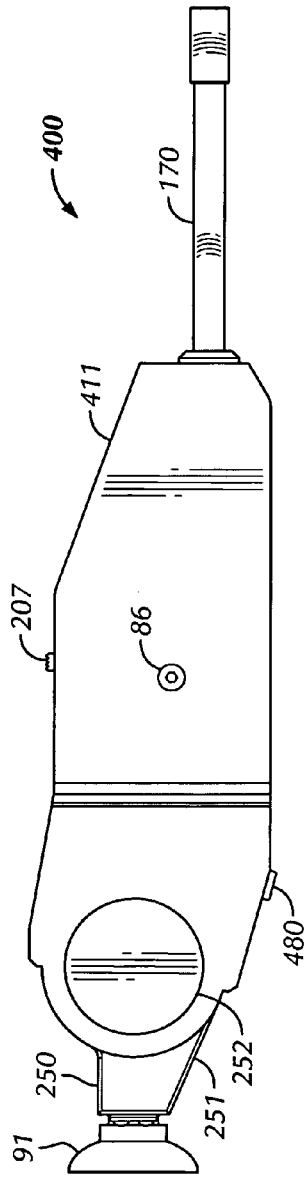
FIG. 18 is a lateral profile view of a fourth embodiment of the examination device.

The lens support assembly 240, shown in FIG. 12, is a pivoting doubly symmetrical linkage which supports a central mirror 310. Reflection of an incoming light beam by the mirror causes the outgoing light beam to be deflected.

The linkage consists of mirror-image righthand and lefthand halves, with the righthand half having both a first 262 and a second 268 righthand link. Likewise, the lefthand half has corresponding first 278 and second 273 lefthand links. The first righthand link 262 and the first lefthand link 278 support a first tubular lens housing 260, while the second righthand link 268 and the second lefthand link 273 support a second tubular lens housing 260. Besides being cojoined by the lens housings 260, the two sides of the lens support assembly 240 are joined in the middle by a mirror carrier 285.

The tubular lens housing 260 consists of a thin wall right circular cylindrical tube having a coplanar transverse pair of flanges slightly offset from a first end which has a small outwardly projecting transverse rim flange. The flanges of the tubular lens housing 260 each have mounting holes 308 engageable by screws 312 for mounting the lens housing 260.

The first lens housing 260, shown on the right side of FIG. 12, contains in sequence from its nonflanged end a first receiving lens 301, a second receiving lens 302, and a third receiving lens 303. The second lens housing 260, shown on the left side of FIG. 12, contains the ocular lens 90 and mounts elastomeric eyecup 91 on its externally protruding annular rim flange.

Referring to FIG. 12, the first righthand link 262 is a flat metal stamping having a first end with a transverse circular pivot hole 263, a straight lower edge, and an outwardly bent flange 264 perpendicular to the lower edge at a second end. The distance from the straight lower edge to the pivot hole 263 is half of the height of the flange 264. The flange 264 is provided with two mounting holes 265 for permitting attachment of a tubular lens housing 260. Parallel to and located adjacent the side of the link 262 opposed to the straight lower edge is an elongated reaction slot 266 which has a close sliding fit to a traveling pin 293. The first lefthand link 278 with its end flange 279 is a mirror image of the first righthand link 262.

The second righthand link 268 is constructed similarly to the first righthand link 262 in having a pivot hole 271, an end flange 269 with mounting holes 270, and a reaction slot 272. Second righthand link 268 is a mirror image of first righthand link 262, except that the flange 269 extends outwardly more and the holes are offset more from the flat main portion of the stamping in order to accommodate mounting a second tubular lens housing when the second righthand link 268 is inwardly set relative to the first righthand link 262 in the lens support assembly 240. The second lefthand link 273 with its end flange 274 is a mirror image of the second righthand link 268.

The mirror carrier 285 is a sheet metal stamping symmetrical about both a midplane corresponding to the midplane of the lens support assembly 240 and a second plane transverse to the midplane. Seen looking down the apparatus midplane, the mirror carrier 285 has a flat rectangular crosspiece 289 transverse to the midplane, with mirror image parallel planar sides equally offset from the midplane. Offset from the crosspiece 289 and located on each side plate in the second plane of symmetry are coaxial pivot holes 286 which are close fits to the two pivot pins 294 of the lens support assembly 240. Extending perpendicularly to the flat crosspiece 289 in the second plane of symmetry and more offset from the crosspiece than the pivot holes 286 are mirror image reaction slots 287, which are close sliding fits to the two traveling pins 293.

Coplanar inwardly extending mirror mounting tabs 288 extend inwardly parallel to the crosspiece 289. Each tab 288 has a central mounting hole for the mirror 310, and the surfaces of the tabs opposed to the crosspiece 289 are parallel. The separation of the tabs 288 is such that, when the mirror 310 is mounted thereon, the upper reflective surface of the mirror is coplanar with the axis of the pivot pins 294 mounted in the pivot holes 286. Access holes are provided in the crosspiece 289 coaxial with the mounting holes in the tabs 288 so that the mirror can be mounted to the tabs.

The mirror 310 is a thin planar rectangular metallic sheet having a highly polished reflective upper surface and side notches to clear the heads of the pivot pins 294. Right circular cylindrical projections on the lower face of the mirror 310 extend through the mounting holes in the tabs 288 of the mirror carrier 285. These projections are peened over to retain the mirror 310 on the mirror carrier.

Flat washers 290 and 292 and also stepped washers 291 are used in the assembly of the lens support assembly 240 to minimize friction between the righthand and lefthand first and second links, 262, 268, 273, and 278 respectively and the mirror carrier 285. The bore of the flat washer 290 is a close fit to the outer diameter of the pivot pin 294. The bore of the flat washer 292 is a close fit to the outer diameter of the traveling pin 293. The bore of the stepped washer 291 is a close fit to the outer diameter of the traveling pin 293, while the diameter of the smaller step of the stepped washer 291 is a sliding fit in the slots of the first and second links 262, 268, 273, and 278 and the mirror carrier 285. Assembly of the linkage shown in FIG. 12 is primarily done using the pivot pins 294 and the traveling pins 293, along with the washers 290 and 291. Both the pivot pins 294 and the traveling pins 293 are peened over on both ends.

When the lens support assembly 240 is assembled, the first tubular lens housing 260 is mounted to the first righthand 262 and the first lefthand 278 links by means of rivets 305 engaged through the mounting holes 308 on the flange 261 of the housing and the corresponding holes 265 of the first righthand link and the first lefthand link.

Next, starting on the near or right side of FIG. 12, a pivot pin 294 is sequentially extended through pivot hole 263 of the first righthand link 262, a flat washer 290, the pivot hole 271 of the second righthand link 268, another flat washer 290, and then a pivot hole 286 of the mirror carrier 285, following which the ends of the cylindrical pins 294 are peened over. The same procedure is then done on the far or left side of FIG. 12 using the first lefthand 278 and second lefthand 273 links.

The next step for the components on the near side of FIG. 12 is to insert a traveling pin 293 sequentially through a stepped washer 291, the reaction slot 266 of the first righthand link 262, a second stepped washer 291, the reaction slot 272 of the second righthand link 268, a third stepped washer, the reaction slot 287 of the mirror carrier 285, and finally through a flat washer 292. The steps of the stepped washer are engaged with the sides of the reaction slots, following which the traveling pin 293 is loosely peened over on both ends. The same procedure is then done on the far side of FIG. 12 using the first lefthand 278, second lefthand 273 link, and the mirror carrier 285.

The final assembly for the rotatable viewing assembly 250 involves combining the second lens housing, the righthand 251 and lefthand 255 covers, and the lens support assembly 240. Referring to FIGS. 8 and 9, the covers 251 and 255 are placed with their circular bosses concentric with the pivot pins 294 of the lens support assembly 240 and with their mating faces lying on the midplane of symmetry of the lens support assembly 240. At the same time, the end of the lens support assembly 240 holding the second lens housing 260 is oriented so that it extends through the cutout in the transverse end face 253 of the lefthand cover 255 and the corresponding cutout of the righthand cover 251. Screws 312 are then extended through the mounting holes 308 of the lens housing 260 and the corresponding holes of the end faces of the covers 251 and 255, and there threadedly engaged with hex nuts 313. The hex nuts 313 are not shown in the illustrations for the third embodiment 200, but can be seen in FIG. 21, wherein the fourth embodiment 400 is illustrated. Fourth embodiment 400 utilizes the same rotatable viewing assembly 250 as does the third embodiment.

V. Fourth Embodiment of the Apparatus

The fourth embodiment 400 of the portable examination device is shown in FIGS. 18 to 22. This fourth embodiment utilizes all of the features of the third embodiment as well as including a means for electronically capturing and transmitting an image which can simultaneously be viewed by eye through the eyepiece lens. Because the housing 411 of the fourth embodiment 400 contains additional features beyond those for the housing 211 of the third embodiment, the changes for housing 411 are discussed below.

The fiber optic system 170, the rotatable viewing assembly 250, the battery 230, the switch 207, and the lens mounting block 450 with its LED and lenses are common to both the third and fourth embodiments. Except as noted below, the two housing halves 412 and 422 are mirror-image parts which surround the internal components of the apparatus 400.

Details of the lefthand housing half 422 are shown in FIGS. 19, 20, and 21. The lefthand housing half 422 is a thin wall body with a vertical outer wall offset from the midplane of the housing assembly and a perpendicular peripheral wall extending normal to the midplane of the housing assembly 411. Housing half 422 has a vertical planar mating face comatable with a corresponding face for righthand housing half 412 at the midplane of the housing assembly. The perpendicular peripheral wall of housing half 422 has a horizontally elongated upper and lower perimeter walls having a rear opening, an intermediate vertical transverse diaphragm 427, and a vertical transverse forward end. The height of the righthand housing half 422 is reduced at its forward end by inclined flat transition sections, with the upper flat transition section extending approximately 40% of the length of the housing half. In the midsection of the lefthand housing half 422, the upper and lower peripheral wall surfaces are parallel and horizontal. At its rear end, the upper and lower peripheral wall surfaces are also parallel, but are inclined upwardly towards the rear.

Offset from the mating face of the lefthand housing half 422 on its forward section is a flat outer wall connected to the perpendicular peripheral wall. The distance between the mating face and the outer wall is less than the height of the lefthand housing half. As can be seen best in FIG. 21, the lefthand housing half 422 is widened toward the rear from the junction of the horizontal portion to the rearwardly upwardly inclined portion of the upper and lower peripheral walls.

The rearward section of the housing half 422, consisting of about one third of its length, has a vertical outer wall which is parallel to but offset more from the vertical housing midplane than the forward end of the housing. The rearward section of the vertical outer wall is arcuate with the axis of the arc horizontal and perpendicular to the midplane of the housing. Coaxial with the axis of the arc on the rearward section of the vertical outer wall is a transverse circular guide bore opening 423. The rearmost section of the vertical outer wall extends farther to the rear than do the upper and lower peripheral walls of the lefthand housing half 422.

As seen in FIG. 21, lefthand housing half 422 has a semicircular cutout wand opening 424 on its forward vertical end which mounts an elastomeric grommet 75 which serves to centralize the fiber optic wand 170 where it passes out of the housing 411. On the upper horizontal side of the housing half 422 is located a rectangular cutout 433 for accommodating the switch 207 for the electric power.

As shown herein, the lefthand housing half 422 has on the inner side of its peripheral walls multiple alignment bosses 426 which extend horizontally past the vertical mating face of the housing half but which do not extend beyond the inner side of the peripheral wall in an outward direction. These alignment bosses 426 serve to maintain alignment between the two housing halves 412 and 422. The alignment bosses represent the only departure from mirror imagery for the two housing halves 412 and 422.

The mounting boss 436 for the beam splitter assembly is approximately square in outline, extends towards the midplane of the housing 411, and has its horizontal centerline aligned with the semicircular image fiber cutout 428, described below. The mounting boss 436 has corner rims to locate the beam splitter assembly 470.

The vertical transverse bulkhead 427 of housing half 422 is provided with horizontal axis semicircular cutouts 409, 428 and 429 which have their axes on the mating plane of the housing half. Cutout 428 serves as a locator and passageway for the image fiber 172 and cutout 429 serves the same purpose for the main fiber bundle 171 of the fiber optic assembly 170. Cutout 409 serves as a passage for one or more battery cables 231.

All of the semicircular cutouts 424, 409, 428, and 429 have the axes of the semicircles on the mating plane of the housing halves 412 and 422. Another semicircular cutout 430 is provided on the lower inclined face of lefthand housing half 422, again with its axis perpendicular to the lower inclined face and located on the housing midplane. Cutout 430 is a close fit to an image data plug 480.

Bosses are provided on the interior vertical faces of the flat outer wall to locate internal components housed within the housing 411. For lefthand housing half 422, inwardly projecting boss 402 locates switch 207, multiple bosses 403 locate the battery 230, and a low height boss 404 extends inwardly above the interior horizontal lower wall of housing 422 to locate the lens mounting block 450.

In addition, two restraining bosses 416 project from the interior vertical wall towards the housing midplane symmetrically positioned about a horizontal plane passing through the axis of guide bore opening 423. The bosses 416 closely fit around the upper and lower edges of the first righthand link 262 of the lens support assembly 240 of the rotatable viewing subassembly 250, thereby locating that assembly. The corresponding bosses of the righthand housing half 412 likewise closely engage the upper and lower edges of the first lefthand link 278 of the lens support assembly 240 of the rotatable viewing subassembly 250.

Corresponding coaxial horizontal holes 437 and 432 penetrate the vertical outer walls of both the righthand 412 and lefthand 422 housing halves, respectively. Hole 432 is hexagonal in order to closely engage and thereby provide rotational restraint for nut 87. These coaxial holes permit the housing screw 86 to extend through both holes and to there engage housing nut 87 so that the housing halves can be assembled into alignment and clamped together.

A beam splitting assembly 470 is shown in a longitudinal vertical cross-section in FIGS. 22-24. The beam splitting assembly 470 is shown in FIG. 22. The beam splitting assembly has a hollow cubic box body 471 with a circular entry port 472 on a first vertical side, a circular through exit port 473 on a second vertical side opposed to the first side, and a third CCD port 474 on its bottom side.

The first embodiment of the beam splitting assembly 470 shown in FIG. 22 has a light filter 477 which passes only a selected range of incident wavelengths mounted concentrically on the exterior side of the entry port 472. The second embodiment of the beam splitting assembly 470 shown in FIG. 23 has a light filter 498 which passes only a selected range of incident wavelengths mounted concentrically on the exterior side of the exit port 473. The third embodiment of the beam splitting assembly 470 shown in FIG. 24 has a light filter 489 which passes only a selected range of incident wavelengths mounted concentrically on the exterior side of the CCD port 474. Different embodiments of the beam splitting assembly may have one, two or three light filters such that a filter covers the entry port, the exit port, the CCD port, any two of the ports, or all three of the ports.

An upper rectangular corner bracket boss 475 is located at the intersection of the top and first side, while a lower rectangular corner bracket boss 475 is located at the intersection of the bottom and the second side. A diagonal groove extends through the corner bracket bosses 475 from the corner of the first vertical side to the corner of the second vertical side and the bottom. The diagonal groove is inclined about 45° from the vertical.

A rectangular beam splitter 476 is mounted in the diagonal grooves of the corner bracket bosses 475 so that it is exposed to incident light entering through the entry port 472 with or without an optional filter 477 mounted thereon. The beam splitter 476 splits the light beam conditioned by the second lens unit 65 into two light beams. One light beam is directed to the ocular viewer 90 and the second beam is directed to an image capture device. Examples of a suitable beam splitter 476 include without limitation a dichroic mirror, a half silvered mirror, or a polarization beam splitter.

A rectangular CCD imaging device or image capture device 478 is mounted to the bottom surface of the body 471 of the beam splitter assembly 470. The beam splitter 476 is selectively constructed to reflect certain incident wavelengths of light downwardly through the CCD port 474, while it passes the remaining wavelengths of incident light through the beam splitter 476 and out through the exit port 473 without reflection. The light reflected downwardly by the beam splitter 476 impinges on the upper, sensitive surface of the charge-coupled device (CCD) 478, whereby a pixelated electronically sensed image is gathered and transmitted to a multiconductor image data plug 480 by image data cable 481. If power is required for the CCD device 478, it can be delivered either by the battery 230 or by means of the multiconductor image data plug 480 and image data cable 481.

The beam splitter assembly 470 allows the operator of the examination device to visualize the tissue and at the same time to capture an image of the tissue 5. The beam splitter assembly 470 can be constructed such that the operator visualizes the same image as the image capture device captures, or it can be constructed such that the operator visualizes a different image than captured by the image capture device. For example, the operator may visualize a reflected image of the tissue, while the CCD image capture device 478 captures an electronic image of tissue autoflourescence at a predetermined wavelength.

OPERATION OF THE APPARATUS EMBODIMENTS

The operation of the portable examination device will vary somewhat depending on the components selected, the configuration of the components, and the tissue to be examined.

By way of example, the portable examination devices of the first 10 and second 100 embodiments function in the following manner. Electrical power is obtained from a wall outlet and is stepped down and rectified to a voltage suitable for the illumination source 2 or LED or laser 57.

The illumination source 2, such as the LED or laser 57, produces a characteristic light spectrum beam 81 which may be conditioned by the lenses and/or filters of the first lens unit 60 prior to being transmitted into main fiber optic bundle 71.

The embodiment illustrated in FIG. 26 uses a single filter/lens to condition the light beam 81, while the embodiment shown in FIGS. 3 and 4 uses both lenses and a filter to prepare the light used to illuminate the tissue 5. Any number of filters and/or lenses may be used to condition the light beam 81. Examples of such filters and/or lenses include a polarizer, a neutral density filter, a fluorescent filter, or a collimating lens may be used.

For example, the first lens unit 60 illustrated in FIG. 4 collimates the light beam 81 with lenses 62 and 63 and then filters the collimated light beam 81 with filter 64 coaxially mounted with the first lens unit 60. The conditioned light beam 81 is then transmitted into the main fiber optic bundle 71 of the fiber optic assembly 70 and directed toward the biological tissue 5 located adjacent the outer end of the fiber optic assembly 70. The second embodiment 100 operates in substantially the same way. The conditioned light beam 81 is similarly transmitted into main fiber bundle 171 of the second embodiment 100 to be directed toward the biological specimen of interest located adjacent the outer end of the fiber optic assembly 170.

Fluorescent and/or reflectance spectra are typically used to characterize the pre-cancerous or cancerous condition of the tissue being examined. One or more excitation fluorescence bandwidths may be used, such as 455-465 nm, 410-430 nm, 375-385 nm and/or 340-360 nm, to excite the tissue. Similarly if reflectance is used to examine the tissue, then white light (400-700 nm), or narrower bands such as 455-465 nm, 410-430 nm or 550-590 nm may be used to illuminate the tissue. Parallel and/or cross-polarized light may also be used to enhance different tissue structures.

At times the second lens unit is configured to substantially block the wavelength band of light selected by the first lens unit. This is particularly useful when the illuminating light beam is selected to excite the autoflourescence of the tissue.

When the portable examination device is in clinical use, a close fitting tubular transparent disposable plastic sanitary sheath 76 for the first embodiment 10 or sheath 176 for the second embodiment 100 is used. The sheaths 76 and 176 have a thin transverse distal end interposed over the distal end of the shaft of the fiber optic assembly for sanitary reasons. The distal tip 77 of the sheath 76 or the distal tip 177 of the sheath 176 are used to contact the tissue of interest rather than the distal end of the shaft of the fiber optic assembly. Using a disposable sheath helps to protect the fiber optic assembly, as well as helping to prevent the spreading of infectious agents from one patient to another.

The distal tip 77 of the sanitary sheath 76 is angled to direct specular reflection from the tissue/sheath interface away from the collection path. Furthermore, an optional lens or optical coupler 178 may be incorporated into the distal tip 77 of the sheath 76. If the distal tip 77 has a lens/optical coupler 78 then the optical coupler 78 will contact the tissue as part of the distal tip 77. Similarly, an optional lens or optical coupler 178 may be incorporated into the distal tip 177 of the sheath 176. If the distal tip 177 has a lens/optical coupler 178 then the optical coupler 178 will contact the tissue as part of the distal tip 177.

The plastic of the disposable sanitary sheath is selected so that it is transparent to the wavelength band of light used to illuminate the sample, as well as the wavelength band of light used to visualize the illuminated tissue. Furthermore, the plastic of the sheath must not autofluoresce or otherwise interfere with the optics and spectral characteristics necessary for the optimal operation of the examination device.

The light beam 82 emanating from the illuminated tissue 5 has a different spectral content that the incident light, depending on the character of the cells illuminated in the specimen. Typically, a liquid contrast agent is applied to the specimen prior to examination with the portable examination device of the present invention. The contrast agent either alters the light reflectance of any cells of interest in the specimen or causes them to fluoresce. Other contrast agents may be configured to bind to specific molecules on cell surfaces such as proteins or receptors.

The reflected or fluoresced light is transmitted by the image fiber 72 or 172 to an ocular viewer. The light beam 82 may be conditioned, for example collimated and filtered, by the second lens set 65 before being directed to the ocular viewer 90, where it is viewed by the operator of the examination device.

The third 200 and fourth 400 embodiments of the present invention function in substantially the same manner as the first two embodiments 10 and 100, but the embodiments 200 and 400 are both provided with an operator adjustable mirror mechanism, the rotatable viewing subassembly 250, which permits the operator to view the specimen image from a position off the axis of the housing and fiber optic assembly 170.

For the third and fourth embodiments 200 and 400, the light from the illumination source or LED 57 is transmitted as light beam 295 to the tissue to be examined. The returning light is conditioned by the second lens unit 65. When the light beam 296 emerges from the second lens unit 65, it is directed at a mirror 310. The mirror 310 is mounted in a lens support assembly 240 which can selectably swivel the second outlet lens housing or holder 260 through a variety of angles while holding the first inlet lens housing 260 static. Thus, the mirror 310 is caused to rotate half as much by the lens support assembly 240 as the second outlet lens holder 260 so that the light beam 296 impinging on the mirror 310 is directed as light beam 297 to the second lens housing 260 and the ocular viewer 90 mounted thereon. The ocular viewer is angularly adjustable up to 90° from the axis of the second lens unit 65.

The fourth embodiment 400 of the present invention interposes a beam splitter assembly 470 between the second lens unit 65 and the selectably rotatable mirror 310 of the rotatable viewing subassembly 250. The beam splitter 476 reflects a certain wavelength band of incident light 492 onto a CCD imaging device 478, while passing the remnant of incident light 493 through the beam splitter 476 without reflection to the mirror 310 of the rotatable viewing subassembly 250 and then to the operator through viewing lens 90. Since a portion of the light beam 491 emanating from the illuminated tissue is reflected onto the CCD imaging device, the operator is permitted to capture an electronic image of the same tissue as being viewed by the operator. The electronically captured image can be electronically stored, enlarged, viewed, and/or spectrally analyzed at any time on an external viewer, processor, and/or computer.

Although the present invention and its advantages have been described in detail, it should be understood that various changes, substitutions and alterations can be made herein without departing from the spirit and scope of the invention as defined by the appended claims.

What is claimed is:

1. A medical examination device for spectrally screening tissue for cancer having:
   an illumination source transmitting a light beam through a first lens unit to condition the light beam;
   a fiber optic bundle including an excitation fiber and an image fiber, wherein the excitation fiber delivers the conditioned light beam from the first lens unit to a tissue to be examined and wherein the image fiber directs a light emanating from an illuminated tissue to a second lens unit;

an angularly adjustable visualization unit having a pivotable linkage with a first lens holder mounted on a first end of the pivotable linkage, a second lens holder mounted on a second end of the pivotable linkage, a pivoting mechanism positioned between the first and second ends of the linkage that allows an operator to adjust an angle of the first lens holder in relationship to the second lens holder, and a mirror rotatably supported by the pivotable linkage proximal the pivoting mechanism such that a light beam conditioned by the second lens unit passes through the angularly adjustable visualization unit and is visualized by the device operator through a lens mounted in a second lens holder and wherein the first lens holder is held in an aligned position that is coaxially aligned with the second lens unit while the mirror and the second lens holder are angularly adjustable about the aligned position.

2. The medical examination device of claim 1, wherein the angularly adjustable visualization unit includes an ocular viewer and an image capture device.

3. The medical examination device of claim 2, wherein the angularly adjustable visualization unit includes a beam splitter between the second lens unit and the ocular viewer.

4. The medical examination device of claim 3, wherein the beam splitter splits a light conditioned by the second lens unit into two light beams with one light beam directed to the ocular viewer and a second beam of light directed to the image capture device.

5. The medical examination device of claim 4, wherein the beam splitter is a dichroic mirror.

6. The medical examination device of claim 1, wherein the first lens unit includes a collimating lens.

7. The medical examination device of claim 1, wherein the first lens unit includes a lens or a filter.

8. The medical examination device of claim 1, wherein the first lens unit includes as polarizing filter.

9. The medical examination device of claim 1, wherein the first lens unit selects a wavelength band of 455-465 nm, 410-465 nm, 375-385 nm, or 340-360 nm.

10. The medical examination device of claim 1, further comprising a disposable sheath for covering the fiber optic bundle.

11. The medical examination device of claim 10, wherein the disposable sheath has a transverse distal end for contacting the tissue to be examined.

12. The medical examination device of claim 1, wherein as distal end of the fiber optic bundle is angled.

13. The medical examination device of claim 12, further comprising an angled disposable sheath for covering the distal end of the fiber optic bundle.

14. The medical examination device of claim 1, wherein the first lens holder is angularly adjustable up to a 90° angle from a position coaxially aligned with the second lens unit.

15. The medical examination device of claim 1, wherein the pivotable linkage including a first side having a first and a second link and a second side having a first and a second link.

16. The medical examination device of claim 15, wherein the first lens holder is mounted on a proximal end of the second link of the first side and a proximal end of the second link of the second side and the second lens holder mounted on a distal end of the first link of the first side and a distal end of the first link of the second side and wherein the pivoting mechanism interconnects the first and second sides of the pivotable linkage between the first and second lens holders.

17. The medical examination device of claim 15, wherein the pivoting mechanism includes a reaction slot in the first and second sides of the pivotable linkage connected with a slideable traveling pin passing through the reaction slot of the first and second sides of the pivotable linkage.

18. The medical examination device of claim 1, wherein a mirror carrier is angularly adjusted by the angular adjustment of the second lens holder such that the second light beam is reflected off the mirrored surface to the second lens holder whenever the second lens holder is angularly adjusted to be out of alignment with the second lens unit.

19. A medical examination device for spectral detection of cancer having:
an illumination source;
a first lens unit conditioning a light beam from the illumination source;
an excitation optic fiber delivering conditioned light beam from the first lens unit to a tissue to be examined;
an image optic fiber receiving a light beam emanating from a tissue illuminated with a conditioned light beam and transmitting a emanated light beam through a second lens unit; and
a viewing assembly having
a pivotable linkage including a first side having a first and second link and a second side having a first and second link,
a first lens holder mounted on a proximal end of the second link of the first side and a proximal end of the second link of the second side,
a second lens holder mounted on a distal end of the first link of the first side and a distal end of the first link of the second side,
a pivoting mechanism interconnecting the first and second sides of the pivotable linkage wherein the pivoting mechanism allows an operator to adjust a angle of the first lens holder in relationship to the second lens holder, and
a mirror carrier having a mirrored surface rotatably supported by an interior end of the first and second links of the first and second sides proximal the pivoting mechanism, wherein the first lens holder is held in an aligned position that is coaxially aligned with the second lens unit while the mirror carrier and the second lens holder are angularly adjustable about the aligned position; and
whereby the emanating light beam passing through the second lens unit is directed through the viewing assembly.

20. The medical examination device of claim 19, wherein the image optic fiber is a coherent fiber optic bundle.

21. The medical examination device of claim 19, further comprising a beam splitter and an image capture device.

22. The medical examination device of claim 21, wherein the beam splitter is positioned between the second lens unit and the viewing assembly.

23. The medical examination device of claim 21, wherein the beam splitter splits the light passing through the second lens unit into two light beams with one light beam directed through the viewing assembly and a second beam of light directed to the image capture device.

24. The medical examination device of claim 19, wherein the first lens unit includes a collimating lens.

25. The medical examination device of claim 19, wherein the first lens unit selects a wavelength band of 455-465 nm, 410-465 nm, 375-385 nm, or 340-360 nm.

26. The medical examination device of claim 25, wherein the second lens unit substantially blocks the wavelength band selected by the first lens unit.

27. The medical examination device of claim 19, further comprising a disposable sheath for covering a distal end of the excitation optic fiber and a distal end of the image optic fiber.

28. The medical examination device of claim 27, wherein the disposable sheath is angled at the distal end.

29. The medical examination device of claim 27, wherein the disposable sheath has an optical coupler incorporated in the distal end.

30. The medical examination device of claim 19, wherein the second lens holder is angularly adjustable up to a 90° angle from the aligned position.

31. A medical examination device having:
an illumination source;
a first lens unit conditioning a light beam from a illumination source;
an excitation optic fiber delivering a conditioned light beam from the first lens unit to a tissue to be examined;
an image optic fiber receiving a light beam emanating from a tissue illuminated with a conditioned light beam and transmitting the emanated light beam through a second lens unit;
a beam splitter that splits the emanated light beam from the second lens unit into a first light beam and a second light beam;
an image capture device for selectably capturing the first light beam; and
a viewing assembly having
a pivotable linkage including a first side having a first and second link and a second side having a first and second link,
a first lens holder mounted on a proximal end of the second link of the first side and a proximal end of the second link of the second side,
a second lens holder mounted on a distal end of the first link of the first side and a distal end of the first link of the second side,
a pivoting mechanism interconnecting the first and second sides of the linkage between the first and second lens holders wherein the pivoting mechanism allows an operator to adjust the angle of the first lens holder in relationship to the second lens holder, and
a mirror carrier having a mirrored surface is rotatably supported by an interior end of the first and second links of the first and second sides proximal the pivoting mechanism, wherein the first lens holder is held in an aligned position that is coaxially aligned with the second lens unit while the mirror and the second lens holder are angularly adjustable about the aligned position; and wherein the second light beam is directed through the viewing assembly to a lens mounted in the second lens holder for visualization of the second light beam by the operator.

32. The medical examination device of claim 31, wherein the mirror carrier is angularly adjusted by the angular adjustment of the second lens holder such that the second light beam is reflected off the mirrored surface to the second lens holder whenever the second lens holder is angularly adjusted to be out of alignment with the second lens unit.

33. The medical examination device of claim 31, wherein the first lens unit selects a wavelength band of 455-465 nm, 410-465 nm, 375-385 nm, or 340-360 nm.

34. The medical examination device of claim 33, wherein the second lens unit substantially blocks the wavelength band selected by the first lens unit.

35. The medical examination device of claim 31, further comprising a disposable sheath for covering a distal end of the excitation optic fiber and a distal end of the image optic fiber.

36. The medical examination device of claim 35, wherein the disposable sheath is angled at the distal end.

37. The medical examination device of claim 35, wherein the disposable sheath has an optical coupler incorporated in the distal end.

38. The medical examination device of claim 35, wherein the disposable sheath has a transverse distal end for contacting the tissue.

39. The medical examination device of claim 31, wherein the second lens holder is angularly adjustable up to a 90° angle from the aligned position.

* * * * *